United States Patent [19]

Stubenrauch et al.

[11] 4,158,559

[45] Jun. 19, 1979

[54] SUBSTITUTED 2,1,3-BENZOTHIADIAZINE COMPOUNDS

[75] Inventors: Gerd Stubenrauch, Ludwigshafen; Gerhard Hamprecht, Mannheim; Bruno Wuerzer, Limburgerhof; Guenter Retzlaff, Roemerberg, all of Fed. Rep. of Germany

[73] Assignee: BASF Aktiengesellschaft, Fed. Rep. of Germany

[21] Appl. No.: 851,781

[22] Filed: Nov. 15, 1977

[30] Foreign Application Priority Data

Dec. 11, 1976 [DE] Fed. Rep. of Germany ....... 2656289

[51] Int. Cl.$^2$ .................... C07D 285/16; A01N 9/14
[52] U.S. Cl. ........................................ 71/91; 71/90; 544/11

[58] Field of Search .................. 544/11; 71/90, 91

[56] References Cited

U.S. PATENT DOCUMENTS

| 3,217,001 | 11/1965 | Santilli et al. | 544/11 |
| 3,940,389 | 2/1976 | McKendry et al. | 544/11 |
| 4,051,130 | 9/1977 | McKendry et al. | 544/11 |
| 4,054,440 | 10/1977 | McKendry et al. | 544/11 |

*Primary Examiner*—John M. Ford
*Attorney, Agent, or Firm*—Keil & Witherspoon

[57] ABSTRACT

New and valuable substituted 2,1,3-benzothiadiazine compounds having a good herbicidal action, herbicides containing these active ingredients, methods of controlling the growth of unwanted plants with these compounds, and processes for manufacturing them.

12 Claims, No Drawings

SUBSTITUTED 2,1,3-BENZOTHIADIAZINE COMPOUNDS

The present invention relates to new and valuable substituted 2,1,3-benzothiadiazine compounds having a good herbicidal action, herbicides containing these active ingredients, and methods of controlling the growth of unwanted plants with these compounds.

It is known that 3-isopropyl-2,1,3-benzothiadiazin-(4)-one-2,2-dioxide and 1-methyl-3-isopropyl-8-methyl-2,1,3-benzothiadiazin-(4)-one-2,2-dioxide have a herbicidal action (German Pat. No. 1,542,836, German Laid-Open Application DOS No. 2,443,901).

We have now found that compounds of the formula

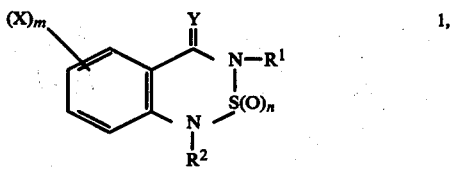

where $R^1$ denotes alkyl, haloalkyl, cycloalkyl, alkenyl, alkynyl, haloalkenyl, haloalkynyl, alkoxyalkyl, alkylmercaptoalkyl, alkyl- and dialkylcarbamoylalkyl, alkoxycarbonyl, alkoxycarboalkyl, alkoxycarboalkenyl, dialkylketone, unsubstituted aryl, aryl substituted by halogen, methyl and/or halomethyl, or $R^1$ denotes a heterocyclic ring, $R^2$ denotes the radicals CN, SCN,

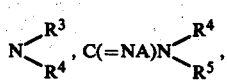

$C(=N-OR^4)R^3$, $S(O)_kR^3$, $S(=O)OR^3$, $S(=O)_2OR^3$, $Si(R^6)_2R^7$,

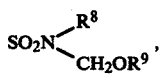

or $SCCl_2F$, X denotes halogen, $NO_2$, lower alkyl, halo lower alkyl, cycloalkyl, arylalkyl, aryl, CN, SCN, $CO_2R^3$,

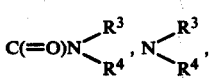

$Y'R^4$, $SO_2R^3$, $SO_2OR^3$,

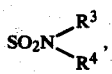

$CCl_3$, $CF_3$, $C(=O)R^3$ or $Y''CF_2C(Z)_3$, $R^3$ denoting hydrogen, lower alkyl, unsubstituted aryl, or aryl substituted by halogen, methyl or nitro, $R^4$ and $R^5$ being identical or different and each having the meanings of $R^3$ and additionally denoting, but not simultaneously, dialkylketone, $R^6$ and $R^7$ being identical or different and each having the meanings of $R^3$ with the exception of hydrogen, $R^8$ and $R^9$ being identical or different and each having the meanings of $R^3$ with the exception of hydrogen and aryl, A having the meanings of $R^3$ or denoting $OR^3$, $N(R^3)_2$, $OC(=O)NHR^3$ or $OC(=O)R^3$, each Y, Y' and Y'' independently denoting oxygen or sulfur, each Z independently denoting hydrogen, fluorine, bromine, chlorine or iodine, and k denoting one of the integers 0 and 1, m denotes one of the integers 0, 1, 2, 3 and 4, and n denotes one of the integers 1 and 2, are good herbicides which, particularly as selective herbicides, have a superior action to prior art compounds.

The new benzothiadiazine compounds of the formula 1 are obtained by reacting compounds of the formula

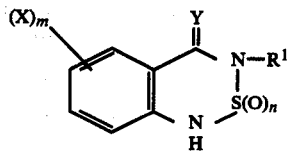

where $R^1$, X, Y, m and n have the above meanings, with a halogen compound of the formula $$Hal-R^2 \qquad 3,$$

where $R^2$ has the above meanings and Hal denotes a halogen atom, in the presence or absence of an acid binder and of an inert solvent, or by reacting salts of compounds of the formula 2 with halogen compounds in the presence or absence of an inert solvent. The starting compounds of the formula 2 are obtained by known methods, for example from substituted anthranilic acid derivatives and substituted sulfamic acid halides. A 1CN derivative obtained in this manner may if desired be further reacted with hydroxylamine.

Examples of meanings for $R^1$ are: hydrogen, methyl, ethyl, n-propyl, isopropyl, cyclopropyl, n-butyl, isobutyl, tert.-butyl, cyclobutyl, n-pentyl, 2-pentyl, 3-pentyl, tert.-amyl, neopentyl, 2-methylbutyl, 3-methylbutyl, 3-methyl-2-butyl, cyclopentyl, n-hexyl, 4-methyl-2-pentyl, 2,3-dimethylbutyl, 2-methyl-1-pentyl, 2-hexyl, 3-hexyl, 3-methyl-2-pentyl, 3-methylpentyl, 4-methylpentyl, 3-methyl-3-pentyl, 4,4-dimethylbutyl, cyclohexyl, heptyl, 2-heptyl, 3-heptyl, 4-heptyl, cycloheptyl, 1-octyl, 2-octyl, 3-octyl, 4-octyl, 5-octyl, 5-ethyl-2-heptyl, 2,6-dimethyl-4-heptyl, 7-ethyl-2-methyl-4-nonyl, 2,4-dimethyl-3-pentyl, 3-methyl-2-heptyl, 5-ethyl-2-nonyl, nonyl, decyl, undecyl, dodecyl, tridecyl, tetradecyl, pentydecyl, hexadecyl, heptadecyl, octadecyl, nonadecyl, eicosyl, 6-ethyl-3-decyl, 6-ethyl-3-octyl, 2-methyl-2-pentyl, 2,3-dimethyl-2-butyl, 2-methyl-2-hexyl, 3-ethyl-3-pentyl, 3-methyl-3-hexyl, 2,3-dimethylpentyl-3, 2,4-dimethyl-2-pentyl, 2,2,3-trimethyl-3-butyl, 2-methyl-2-heptyl, 4-methyl-4-heptyl, 2,4-dimethyl-2-hexyl, 2-methyl-2-octyl, 1-methyl-1-cyclopentyl, 1-methyl-1-cyclohexyl, 1-ethyl-1-cyclohexyl, chloro-tert.-butyl, 1,1-dichloro-2-methyl-2-propyl, 1,3-dichloro-2-methyl-2-propyl, 1-cyclohexyl-1-ethyl, 1-chloroethyl, 2-chloroethyl, 1-chloropropyl, 2-chloropropyl, 3-chloropropyl, 1-chloro-2-propyl, 2-chlorobutyl, 2-chloro-2-methyl-3-propyl, 1-fluoroethyl, 2-fluoroethyl, 2-fluoropropyl, 3-fluoropropyl, 1-fluoro-2-propyl, 2-fluorobutyl, 2-fluoro-2-methyl-3-propyl, 2-bromoethyl, 3-bromopropyl, 4-chlorobutyl, 2-chlorocyclohexyl, 1,1,1-trifluoroisopropyl, hexafluoro-2-methylisopropyl, hexafluoroisopropyl, hexachloroisopropyl, 1,2-dibromoallyl, 2,2,2-trifluoroethyl, 1-chlorobutyn-2-yl-4, 3-chlorobutyn-1-yl-4, 1-chlorobuten-2-yl-4, 2,3-dibromo-1-propyl, 2,2,2-trichloroethyl, 1-chloropentyn-2-yl-4, 2,2,2-tribromoethyl, 3,4,4-trichlorobuten-3-yl-2, 1-bromo-2-propyl, 1,3-dibromo-2-propyl, 3-chlorobuten-1-yl-4, allyl, methallyl, crotyl, 2-ethylhexen-2-yl-1, hexen-5-yl- 1, undecen-10-yl-1, 2-methylbuten-2-yl-1, 2-methylbuten-1-yl-3, butyn-1-yl-3, butyn-2-yl-1, buten-1-yl-3, propargyl, 2-methylbuten-1-yl-4, 2-methylbuten-2-yl-4, 3-methylbuten-1-yl-3, 1-ethynylcyclohexyl, methoxyethyl, ethoxyethyl, 3-methoxypropyl, methoxyisopropyl, 3-methoxybutyl, 1-methoxybutyl-2, ethoxy-tert.-butyl, methoxy-tert.-butyl, cyclohexoxytert.-butyl, 2-methoxybutyl, 4-methoxybutyl, methylmercaptoethyl, ethylmercaptoethyl, 3-methylmercaptopropyl, 3-methylmercaptobutyl, 1-methylmercaptobutyl-2, methylmercapto-tert.-butyl, 2-methylmercaptobutyl, 4-methylmercaptobutyl, 3-n-butoxyethyl, 2-ethoxypropyl, 3-ethoxy-2-propyl, 2-methylbutanon-3-yl-2, 2-methylpentanon-4-yl-2, 3-butanon-1-yl, 3-butanon-2-yl, 2-propanon-1-yl, 2-pentanon-1-yl, methyl acetate-2, ethyl acetate-2, methyl propionate-2, methyl propionate-3, methyl butyrate-2, methyl butyrate-3, methyl butyrate-4, methyl-(2-vinyl propionate-2), methyl-(2-vinyl acetate-2), methylcarbamoylmethyl, dimethylcarbamoylmethyl, phenyl, o-tolyl, m-tolyl, p-fluorophenyl, m-fluorophenyl, p-chlorophenyl, p-tolyl, o-chlorophenyl, o,p-dichlorophenyl, o,p-difluorophenyl, m-trifluoromethylphenyl, o-fluorophenyl, 3,5-dimethylphenyl, 3,5-dichlorophenyl, p-bromophenyl, m-bromophenyl, 3,5-difluorophenyl and pyrrolidinyl.

Examples of meanings for $R^2$ are: cyano, thiocyanato, guanyl, $N^2$-methylguanyl, $N^2$-ethylguanyl, $N^1$-ethyl-$N^1$-methyl-$N^2$-phenylguanyl, $N^1$-methylguanyl, $N^1$-isopropylguanyl, $N^1,N^1$-dimethylguanyl, $N^1,N^1,N^2$-trimethylguanyl, $N^2$-hydroxyguanyl, $N^2$-methoxyguanyl, $N^1$-isopropyl-$N^2$-methoxyguanyl, $N^1$-methyl-$N^1$-propyl-$N^2$-methoxyguanyl, $N^2$-methylcarbamoyloxyguanyl, $N^2$-acetoxyguanyl, $N^1,N^1$-dimethyl-$N^2$-acetoxyguanyl, $N^1,N^1$-dimethyl-$N^2$-aminoguanyl, $N^1,N^1$-dimethyl-$N^2$-dimethylaminoguanyl, methanecarbohydroximoyl, benzohydroximoyl, ethanecarbohydroximoyl, O-methylbenzohydroximoyl, O-ethylethanecarbohydroximoyl, O-propylmethanecarbohydroximoyl, amino, dimethylamino, diethylamino, N-isopropyl-N-methylamino, N-ethyl-N-butylamino, methylamino, isopropylamino, sec-butylamino, α-methylpiperidino, methylsulfenyl, ethylsulfenyl, p-chlorophenylsulfenyl, 2,4-dinitrophenylsulfenyl, p-tolylsulfenyl, dichlorofluoromethylsulfenyl, methoxysulfynyl, ethoxysulfynyl, benzyloxysulfynyl, methoxysulfonyl, ethoxysulfonyl, N-methoxymethyl-N-methylsulfamoyl, N-isopropyl-N-methoxymethylsulfamoyl, N-sec-butyl-N-methoxymethylsulfamoyl and trimethylsilyl.

The term "halogen" denotes fluorine, chlorine, bromine and iodine. The terms "lower alkyl" and "halo lower alkyl" denote linear or branched, optionally halogen-substituted alkyl of from 1 to 6 carbon atoms.

The term "cycloalkyl" denotes for instance cyclopropyl, cyclobutyl, cyclopentyl, cyclohexyl and cycloheptyl. The term "aryl" denotes phenyl and substituted phenyl, such as halophenyl or tolyl.

If the starting materials are 3-phenyl-2,1,3-benzothiadiazin-(4)-one-2,2-dioxide and cyanogen bromide, the reaction according to the invention may be represented by the following scheme:

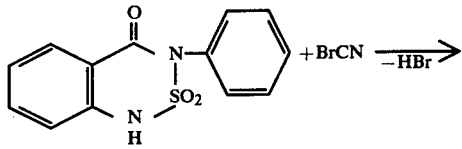

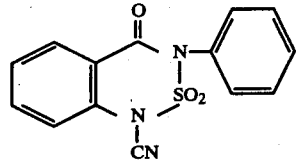

If the starting materials are the sodium salt of 3-isopropyl-2,1,3-benzothiadiazin-(4)-one-2,2-dioxide and N-methoxymethyl-N-methylsulfamoyl chloride, the reaction may be represented by the following scheme:

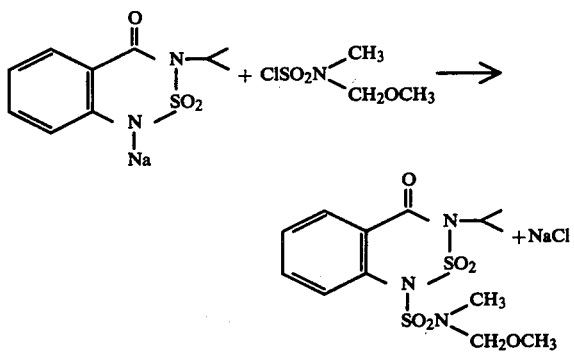

If the starting materials are 1-cyano-3-methyl-2,1,3-benzothiadiazin-(4)-one-2,2-dioxide and hydroxylamine hydrochloride, the reaction may be represented by the following scheme:

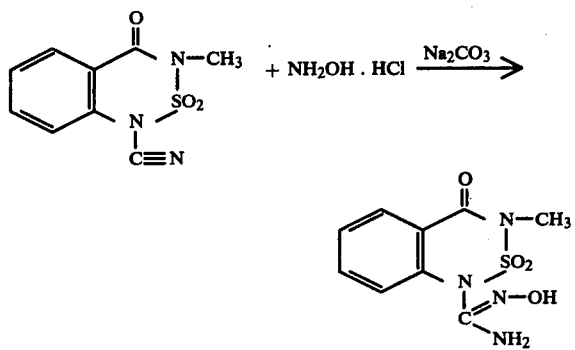

In a preferred embodiment, for instance a 3-alkyl-2,1,3-benzothiadiazin-(4)-one-2,2-dioxide is reacted with a halogen derivative of the formula 3, in the presence or absence of an inert solvent and of an acid binder at from −50° to +120° C., preferably from −20° to +50° C., for from 1 to 20 hours, continuously or batchwise, and at atmospheric or superatmospheric pressure.

Examples of preferred inert solvents in the process of the invention are hydrocarbons such as ligroin, gasoline, toluene, pentane, hexane, cyclohexane and petroleum ether; halohydrocarbons such as methylene chloride, chloroform, carbon tetrachloride, 1,1- and 1,2-dichloroethane, 1,1,1- and 1,1,2-trichloroethane, chlorobenzene, o,m,p-dichlorobenzene and o,m,p-chlorotoluene; nitrohydrocarbons such as nitrobenzene, nitroethane and o,m,p-chloronitrobenzene; nitriles such as acetonitrile, butyronitrile, isobutyronitrile and benzonitrile; ethers such as diethyl ether, di-n-propyl ether, tetrahydrofuran and dioxane; esters such as acetoacetic ester, ethyl acetate and isobutyl acetate; amides such as formamide, methyl formamide and dimethyl formamide; and ketones such as acetone, butanone-2, acetophenone and cyclohexanone. For the reaction with hydroxylamine, alcohols, e.g., ethanol, isopropanol or butanol, may also be used.

The following compounds, for example, may be used as acid binders: sodium carbonate, sodium bicarbonate, triethylamine, pyridine, trimethylamine, $\alpha,\beta,\gamma$-picoline, lutidine, N,N-dimethylaniline, N,N-dimethylcyclohexylamine, quinoline, tri-n-propylamine, n-propyldiisopropylamine and tri-n-butylamine.

Starting materials 2 and 3 may be added in any order. Instead of employing an acid binder, it is possible to remove the hydrogen halide formed during the reaction with an inert gas, e.g., nitrogen. The following procedure is particularly preferred. A solution or suspension of starting material 3 in one of the abovementioned inert solvents is run into a solution or suspension of starting material 2, or a salt thereof, in one of the abovementioned inert solvents; alternatively, starting material 3 is introduced undiluted into the solution or suspension of starting material 2 in one of the abovementioned inert solvents, the acid binder, either undiluted or diluted with one of the abovementioned inert solvents, is then run in, and the reaction carried out in the prescribed temperature range.

In addition to the 2,1,3-benzothiadiazine derivatives of the formula 2, the alkali metal, alkaline earth metal, ammonium or zinc salts derived therefrom may be used as starting materials. The halogen derivatives 3 are advantageously employed in amounts of from 1 to 4, preferably from 1.2 to 1.4, moles per mole of starting compound 2.

To isolate the compounds of the formula 1 from the reaction mixture in accordance with the invention, the reaction mixture is stirred—when water-miscible solvents are used—into a dilute aqueous alkali metal solution. The oil which separates out is if desired extracted and the extract is washed with water and dried. If water-immiscible solvents are used, the reaction mixture may also be extracted direct with dilute alkali metal solution and water. If desired, the reaction mixture may also be concentrated, taken up in a water-immiscible solvent and worked up as described above. The desired end products are obtained by drying and concentrating the organic phase. If desired, they may be further purified in conventional manner, e.g., by recrystallization or chromatography.

EXAMPLE 1

22.6 parts (by weight) of 3-ethyl-2,1,3-benzothiadiazin-(4)-one-2,2-dioxide was dissolved in 100 parts of acetone; while stirring and at 0° C., 12 parts of cyanogen bromide was added and then 11.5 parts by weight of triethylamine was dripped in. The reaction mixture was stirred for 8 hours at 0° C. and for 12 hours at room temperature, the precipitate was filtered off and the organic phase concentrated. 300 parts of methylene chloride was added and extraction carried out twice with 100 parts of 1 N aqueous caustic solution and once with water. After drying over magnesium sulfate, concentration and recrystallization from isopropanol, 18 parts (71% of theory) of 1-cyano-3-ethyl-2,1,3-benzothiadiazin-(4)-one-2,2-dioxide was obtained as colorless crystals; m.p.: 89°–91° C.

EXAMPLE 2

At room temperature and while stirring, 12 parts of cyanogen bromide was added to a suspension of 27.8 parts of the potassium salt of 3-isopropyl-2,1,3-benzothiadiazin-(4)-one-2,2-dioxide in 300 parts of acetonitrile. After the reaction mixture had been stirred for 20 hours, it was concentrated, poured into 300 parts of water, and extracted with 200 parts of methylene chloride. The organic extract was washed with saturated sodium bicarbonate solution, dried and concentrated. 1-cyano-3-isopropyl-2,1,3-benzothiadiazin-(4)-one-2,2-dioxide, m.p. 100°–101° C., was obtained by recrystallization from isopropanol.

EXAMPLE 3

22.6 parts of 3-ethyl-2,1,3-benzothiadiazin-(4)-one-2,2-dioxide was dissolved in 150 parts of ethyl acetate; at 20° C., 15 parts of cyanogen bromide and then 14 parts of triethylamine were added. After the mixture had been stirred for 3 hours at room temperature, it was filtered and the filtrate was extracted twice with cold 1 N aqueous caustic soda solution. After drying, the solvent was removed and the residue recrystallized from isopropanol. There was obtained 21.3 parts (85% of theory) of 1-cyano-3-ethyl-2,1,3-benzothiadiazin-(4)-one-2,2-dioxide; m.p.: 89°–91° C.

EXAMPLE 4

7.7 parts of hydroxylamine hydrochloride and 12 parts of anhydrous sodium carbonate were suspended in 300 parts of absolute ethanol and stirred for 30 minutes at room temperature. While cooling, 26.5 parts of 1-cyano-3-isopropyl-2,1,3-benzothiadiazin-(4)-one-2,2-dioxide was introduced and the whole stirred for 4 hours at room temperature. After the reaction mixture had been filtered and concentrated, the residue was dissolved in 500 parts of ethyl acetate and extracted twice with saturated bicarbonate solution. The organic phase was dried, concentrated and recrystallized from toluene; there was obtained 1-($N^2$-hydroxy)-guanyl-3-isopropyl-2,1,3-benzothiadiazin-(4)-one-2,2-dioxide having a melting point of 175° C. (decomposes).

EXAMPLE 5

24 parts of 3-isopropyl-2,1,3-benzothiadiazin-(4)-one-2,2-dioxide was suspended in 150 parts of 1,2-dichloroethane; at 5° to 10° C., 12 parts of cyanogen bromide was added. At this temperature, 14 parts of N,N-dimethylcyclohexylamine was then dripped in and the mixture stirred for 4 hours at room temperature. The solution was then washed twice with cold 1 N aqueous caustic soda solution and once with water, and dried, and the solvent was removed in vacuo. After recrystallization from isopropanol, there was obtained 22 parts (83% of theory) of pure 1-cyano-3-isopropyl-2,1,3-benzothiadiazin-(4)-one-2,2-dioxide, m.p.: 100°–101° C.

EXAMPLE 6

At 0° C., 22.6 parts of 3-ethyl-2,1,3-benzothiadiazin-(4)-one-2,2-dioxide was introduced into a solution of 7 parts of cyanogen chloride in 200 parts of 1,2-dichloroethane. 14 parts of N,N-dimethylcyclohexylamine was then dripped in and the mixture was stirred for 3 hours at room temperature. Subsequently, the mixture was washed twice with cold 1 N aqueous caustic soda solution and once with water, and dried, and the solvent was removed in vacuo. After recrystallization from isopropanol, there was obtained 22 parts (88% of theory) of 1-cyano-3-ethyl-2,1,3-benzothiadiazin-(4)-one-2,2-dioxide; m.p.: 90°–91° C.

Further active ingredients of the formula 1 were prepared analogously. They are listed in the following table, m denoting 0.

TABLE 1

| $R^1$ | $R^2$ | Y | n | m.p.(°C.) |
|---|---|---|---|---|
| $CH_3$ | CN | O | 2 | 102–103 |
| $CH_3$ | SCN | O | 2 | |
| $CH_3$ | $C(=NOH)NH_2$ | O | 2 | |
| $CH_3$ | $C(=NH)N(CH_3)_2$ | O | 2 | |
| $CH_3$ | $C(=N-OCOCH_3)NH_2$ | O | 2 | |
| $CH_3$ | $C(=NOH)C_2H_5$ | O | 2 | |
| $CH_3$ | $SO_2OCH_3$ | O | 2 | |
| $CH_3$ | $Si(CH_3)_3$ | O | 2 | |
| $CH_3$ | $C(=N-OCH_3)NH_2$ | O | 2 | |
| $CH_3$ | $NH_2$ | O | 2 | |
| $CH_3$ | $N(CH_3)_2$ | O | 2 | |
| $CH_3$ | $SC_6H_4\text{-}p\text{-}Cl$ | O | 2 | |
| $CH_3$ | $SCCl_2F$ | O | 2 | |
| $CH_3$ | CN | S | 2 | |
| $CH_3$ | CN | O | 1 | |
| $CH_3$ | $SO_2N(CH_3)(CH_2OCH_3)$ | O | 2 | |
| $C_2H_5$ | $SO_2N(CH_3)(CH_2OCH_3)$ | O | 2 | |
| $C_2H_5$ | $SO_2OCH_3$ | | | |
| $C_2H_5$ | $SC_6H_3\text{-}2,4(NO_2)_2$ | O | 2 | |
| $C_2H_5$ | $SCCl_2F$ | O | 2 | $n_D^{23}=1.5545$ |
| $C_2H_5$ | $NH_2$ | O | 2 | |
| $C_2H_5$ | $NH\text{-}i\text{-}C_3H_7$ | O | 2 | |
| $C_2H_5$ | $C(=NH)N(CH_3)_2$ | O | 2 | |
| $C_2H_5$ | $C(=N-OCH_3)NH_2$ | O | 2 | |
| $C_2H_5$ | $C(=NOCH_3)C_6H_5$ | O | 2 | |
| $C_2H_5$ | CN | S | 2 | |
| $C_2H_5$ | CN | O | 1 | |
| $C_2H_5$ | SCN | O | 2 | |
| $n\text{-}C_3H_7$ | SCN | O | 2 | |
| $n\text{-}C_3H_7$ | $NH_2$ | O | 2 | |
| $n\text{-}C_3H_7$ | $SCCl_2F$ | O | 2 | |
| $n\text{-}C_3H_7$ | $C(=NOH)NH_2$ | O | 2 | |
| $n\text{-}C_3H_7$ | $C(=NOCOCH_3)NH_2$ | O | 2 | |
| $n\text{-}C_3H_7$ | $C(=N-OCH_3)NHCH_3$ | O | 2 | |
| $n\text{-}C_3H_7$ | $SO_2N(CH_3)(CH_2OCH_3)$ | O | 2 | |
| $n\text{-}C_3H_7$ | $C(=N-OH)C_6H_5$ | O | 2 | |
| $n\text{-}C_3H_7$ | $Si(CH_3)_3$ | O | 2 | |
| $n\text{-}C_3H_7$ | CN | O | 2 | 97–98 |
| $i\text{-}C_3H_7$ | CN | S | 2 | |
| $i\text{-}C_3H_7$ | CN | O | 1 | |
| $i\text{-}C_3H_7$ | SCN | O | 2 | |
| $i\text{-}C_3H_7$ | $C(=NH)N(CH_3)_2$ | O | 2 | |
| $i\text{-}C_3H_7$ | $C(=NCH_3)N(CH_3)_2$ | O | 2 | |
| $i\text{-}C_3H_7$ | $C(=NC_2H_5)NHC_3H_7$ | O | 2 | |
| $i\text{-}C_3H_7$ | $C(=N-OCOCH_3)NH_2$ | O | 2 | |
| $i\text{-}C_3H_7$ | $C(=N-OCH_3)NH_2$ | O | 2 | 123 |
| $i\text{-}C_3H_7$ | $C(=NOH)N(CH_3)_2$ | O | 2 | |
| $i\text{-}C_3H_7$ | $C(=NOH)N(CH_3)(C_3H_7)$ | O | 2 | |
| $i\text{-}C_3H_7$ | $C(=N-OCONHCH_3)NH_2$ | O | 2 | 203–204 |
| $i\text{-}C_3H_7$ | $C(=NOH)C_6H_5$ | O | 2 | |
| $i\text{-}C_3H_7$ | $NH_2$ | O | 2 | |
| $i\text{-}C_3H_7$ | $NH_2$ | S | 2 | |
| $i\text{-}C_3H_7$ | $N(CH_3)_2$ | O | 2 | |
| $i\text{-}C_3H_7$ | $N(CH_3)(C_4H_9)$ | | | |
| $i\text{-}C_3H_7$ | $SCCl_2F$ | O | 2 | NMR (CDCl$_3$): CH$_3$ δ 1.55; 1.6; CH 5.05; arom. H 7.2–8.25 |
| $i\text{-}C_3H_7$ | $SC_6H_4\text{-}p\text{-}Cl$ | O | 2 | |
| $i\text{-}C_3H_7$ | $S-C_6H_3\text{-}2,4(NO_2)_2$ | O | 2 | |
| $i\text{-}C_3H_7$ | $S(O)OC_2H_5$ | O | 2 | |
| $i\text{-}C_3H_7$ | $S(O)OCH_3$ | O | 2 | |
| $i\text{-}C_3H_7$ | $SO_2OCH_3$ | O | 2 | |

TABLE 1-continued

| R¹ | R² | Y | n | m.p.(°C.) |
|---|---|---|---|---|
| i-C₃H₇ | SO₂N(CH₃)(CH₂OCH₃) | O | 2 | 119–123 |
| i-C₃H₇ | SO₂N(i-C₃H₇)(CH₂OCH₃) | O | 2 | |
| i-C₃H₇ | SO₂N(sec C₄H₉)(CH₂OCH₃) | O | 2 | |
| i-C₃H₇ | Si(CH₃)₃ | O | 2 | |
| i-C₃H₇ | Si(C₆H₅)₃ | O | 2 | |
| i-C₃H₇ | Si(C₆H₅)₂CH₃ | O | 2 | |
| n-C₄H₉ | SC₆H₄-p-Cl | O | 2 | |
| n-C₄H₉ | SCCl₂F | O | 2 | |
| n-C₄H₉ | SCN | O | 2 | |
| n-C₄H₉ | CN | O | 2 | |
| n-C₄H₉ | C(=NOH)NH₂ | O | 2 | |
| n-C₄H₉ | SO₂N(CH₃)(CH₂OCH₃) | O | 2 | |
| n-C₄H₉ | C(=NOCH₃)C₂H₅ | O | 2 | |
| n-C₄H₉ | NH₂ | O | 2 | |
| n-C₄H₉ | C(=NH)NHCH₃ | O | 2 | |
| sec C₄H₉ | CN | O | 2 | 79–80 |
| sec C₄H₉ | CN | S | 2 | |
| sec C₄H₉ | SCN | O | 2 | |
| sec C₄H₉ | SCCl₂F | O | 2 | |
| sec C₄H₉ | C(=NOH)C₆H₅ | O | 2 | |
| sec C₄H₉ | C(=NOH)NH₂ | O | 2 | 141–143 |
| sec C₄H₉ | NH₂ | O | 2 | |
| CH(C₂H₅)₂ | CN | O | 2 | |
| CH(C₂H₅)₂ | CN | O | 1 | |
| i-C₃H₇ | SO₂N(C₂H₅)(CH₂OCH₃) | O | 2 | $N_D^{25}$ = 1.5300 |
| CH(C₂H₅)₂ | SCN | O | 2 | |
| CH(C₂H₅)₂ | C(=NOCH₃)NH₂ | O | 2 | |
| CH(C₂H₅)₂ | C(=NCH₃)NH₂ | O | 2 | |
| CH(C₂H₅)₂ | S(O)OC₂H₅ | O | 2 | |
| CH(C₂H₅)₂ | SCCl₂F | S | 2 | |
| CH(C₂H₅)₂ | SCCl₂F | O | 2 | |
| CH(C₂H₅)₂ | NH₂ | O | 2 | |
| CH(C₂H₅)₂ | N(CH₃)(C₃H₇) | O | 2 | |
| CH(C₂H₅)₂ | Si(CH₃)₃ | O | 2 | |
| CH(C₂H₅)₂ | SO₂N(CH₃)(CH₂OCH₃) | O | 2 | |
| CH(C₂H₅)₂ | C(=NOH)C₂H₅ | O | 2 | |
| c-C₃H₅ | CN | O | 2 | 118–120 |
| c-C₃H₅ | C(=NOH)NH₂ | O | 2 | |
| c-C₃H₅ | SC₂H₅ | O | 2 | |
| c-C₃H₅ | SO₂OCH₃ | O | 2 | |
| c-C₃H₅ | NH₂ | O | 2 | |
| c-C₃H₅ | SO₂N(CH₃)(CH₂OCH₃) | O | 2 | |

TABLE 1-continued

| R¹ | R² | Y | n | m.p.(°C.) |
|---|---|---|---|---|
| (triangle) | C(=NOH)C₂H₅ | O | 2 | |
| (pentagon)H | NH₂ | O | 2 | |
| (pentagon)H | CN | O | 2 | |
| (pentagon)H | SCN | O | 2 | |
| (pentagon)H | S(O)OCH₃ | O | 2 | |
| (pentagon)H | S—CCl₂F | O | 2 | |
| (pentagon)H | C(=NOCH₃)NH₂ | O | 2 | |
| (pentagon)H | Si(CH₃)₃ | O | 2 | |
| (pentagon)H | C(=NOH)C₆H₅ | O | 2 | |
| (hexagon)H | CN | O | 2 | 116–118 |
| (hexagon)H | CN | S | 2 | |
| (hexagon)H | SCN | O | 2 | |
| (hexagon)H | C(=NH)N(CH₃)₂ | O | 2 | |
| (hexagon)H | C(=NOCH₃)NH₂ | O | 2 | |
| (hexagon)H | SCCl₂F | O | 1 | |
| (hexagon)H | S—C₆H₃-2,4(NO₂)₂ | O | 2 | |
| (hexagon)H | SO₂OC₂H₅ | O | 2 | |

TABLE 1-continued

| R¹ | R² | Y | n | m.p.(°C.) |
|---|---|---|---|---|
| C₆H₁₁ (cyclohexyl) | SO₂N(CH₃)(CH₂OCH₃) | O | 2 | |
| C₆H₁₁ (cyclohexyl) | NH₂ | O | 2 | |
| C₆H₁₁ (cyclohexyl) | C(=NOH)C₆H₅ | O | 2 | |
| CH(CH₃)CH₂CH(CH₃)₂ | Si(CH₃)₃ | O | 2 | |
| CH(CH₃)CH₂CH(CH₃)₂ | SO₂N(CH₃)(CH₂OCH₃) | O | 2 | |
| CH(CH₃)CH₂CH(CH₃)₂ | S(O)OC₂H₅ | O | 2 | |
| CH(CH₃)CH₂CH(CH₃)₂ | SCCl₂F | O | 1 | |
| CH(CH₃)CH₂CH(CH₃)₂ | SCCl₂F | O | 2 | |
| CH(CH₃)CH₂CH(CH₃)₂ | SC₆H₄-p-CH₃ | O | 2 | |
| CH(CH₃)CH₂CH(CH₃)₂ | N(CH₃)(sec C₄H₉) | O | 2 | |
| CH(CH₃)CH₂CH(CH₃)₂ | N(CH₃)₂ | O | 2 | |
| CH(CH₃)CH₂CH(CH₃)₂ | NH₂ | O | 2 | |
| CH(CH₃)CH₂CH(CH₃)₂ | C(=NOH)NH₂ | O | 2 | |
| CH(CH₃)CH₂CH(CH₃)₂ | CN | O | 2 | |
| CH(CH₃)CH₂CH(CH₃)₂ | SCN | O | 2 | |
| CH₂CH₂Cl | CN | O | 2 | 139–140 |
| CH₂CH₂Cl | SCN | O | 2 | |
| CH₂CH₂Cl | C(=NH)NHCH₃ | O | 2 | |
| CH₂CH₂Cl | CN | S | 2 | |
| CH₂CH₂Cl | CN | O | 1 | |
| CH₂CH₂Cl | C(=N—N(CH₃)₂)NHCH₃ | O | 2 | |
| CH₂CH₂Cl | C(=NOH)NH₂ | O | 2 | |
| CH₂CH₂Cl | NH₂ | O | 2 | |
| CH₂CH₂Cl | N(CH₃)(C₄H₉) | O | 2 | |
| CH₂CH₂Cl | SCCl₂F | S | 2 | |
| CH₂CH₂Cl | SCCl₂F | O | 2 | |
| CH₂CH₂Cl | S(O)OCH₃ | O | 2 | |
| CH₂CH₂Cl | SO₂N(CH₃)(CH₂OCH₃) | O | 2 | |
| CH₂CH₂Cl | C(=NOCH₃)C₆H₅ | O | 2 | |
| CH(CH₃)CH=CH—CH₃ | CN | O | 2 | |
| CH(CH₃)CH=CH—CH₃ | SCN | O | 2 | |

TABLE 1-continued

| R¹ | R² | Y | n | m.p.(°C.) |
|---|---|---|---|---|
| CH(CH₃)(CH=CH—CH₃) | C(=NOCH₃)NH₂ | O | 2 | |
| CH(CH₃)(CH=CH—CH₃) | C(=NOH)NH₂ | O | 2 | |
| CH(CH₃)(CH=CH—CH₃) | C(=NH)N(CH₃)₂ | O | 2 | |
| CH(CH₃)(CH=CH—CH₃) | NH₂ | O | 2 | |
| CH(CH₃)(CH=CH—CH₃) | NH-i-C₃H₇ | O | 2 | |
| CH(CH₃)(CH₂F) | SCCl₂F | O | 1 | |
| CH(CH₃)(CH₂F) | SCCl₂F | O | 2 | |
| CH(CH₃)(CH₂F) | S(O)OCH₃ | O | 2 | |
| CH(CH₃)(CH₂F) | SO₂OC₂H₅ | O | 2 | |
| CH(CH₃)(CH₂F) | SO₂N(CH₃)(CH₂OCH₃) | O | 2 | |
| CH(CH₃)(CH₂F) | Si(CH₃)₃ | O | 2 | |
| CH(CH₃)(CH₂F) | C(=NOH)C₂H₅ | S | 2 | |
| CH(CH₃)(CH=CH₂) | CN | O | 2 | |
| CH(CH₃)(CH=CH₂) | SCN | O | 2 | |
| CH(CH₃)(CH=CH₂) | NH₂ | O | 2 | |
| CH(CH₃)(CH=CH₂) | N(CH₃)₂ | O | 2 | |
| CH(CH₃)(CH=CH₂) | SCCl₂F | S | 2 | |
| CH(CH₃)(CH=CH₂) | SCCl₂F | O | 2 | |
| CH(CH₃)(CH=CH₂) | Si(CH₃)₃ | O | 2 | |
| CH(CH₃)(CH=CH₂) | C(=NOCH₃)NH₂ | O | 2 | |
| CH(CH₃)(CH=CH₂) | S(O)OCH₃ | O | 2 | |
| CH(CH₃)(C≡CH) | Si(CH₃)₃ | O | 2 | |
| CH(CH₃)(C≡CH) | SO₂N(CH₃)(CH₂OCH₃) | O | 2 | |
| CH(CH₃)(C≡CH) | SO₂OCH₃ | O | 2 | |
| CH(CH₃)(C≡CH) | SCCl₂F | O | 2 | |

TABLE 1-continued

| R$^1$ | R$^2$ | Y | n | m.p.(°C.) |
|---|---|---|---|---|
| CH(CH$_3$)C≡CH | C(=NOCH$_3$)NH$_2$ | O | 2 | |
| CH(CH$_3$)C≡CH | C(=NCH$_3$)NH$_2$ | O | 2 | |
| CH(CH$_3$)C≡CH | CN | O | 2 | |
| CH(CH$_3$)C≡CH | SCN | O | 2 | |
| CH$_2$—CH=CH$_2$ | SCN | O | 2 | |
| CH$_2$—CH=CH$_2$ | SCCl$_2$F | O | 2 | |
| CH$_2$—CH=CH$_2$ | SCCl$_2$F | O | 1 | |
| CH$_2$—CH=CH$_2$ | S(O)OCH$_3$ | O | 2 | |
| CH$_2$—CH=CH$_2$ | Si(C$_2$H$_5$)$_3$ | O | 2 | |
| CH$_2$—CH=CH$_2$ | NH$_2$ | O | 2 | |
| CH$_2$—CH=CH$_2$ | N(CH$_3$)$_2$ | O | 2 | |
| CH$_2$—CH=CH$_2$ | C(=NOCH$_3$)NH$_2$ | O | 2 | |
| CH$_2$—CH=CH$_2$ | SO$_2$N(CH$_3$)(CH$_2$OCH$_3$) | O | 2 | |
| CH$_2$—CH=CH$_2$ | CN | O | 2 | |
| CH$_2$—CH=CH$_2$ | CN | S | 2 | |
| CH$_2$—C≡CH | CN | O | 2 | |
| CH$_2$—C≡CH | NH$_2$ | O | 2 | |
| CH$_2$—C≡CH | N(CH$_3$)$_2$ | O | 2 | |
| CH$_2$—C≡CH | SCN | O | 2 | |
| CH$_2$—C≡CH | SCCl$_2$F | O | 2 | |
| CH$_2$—C≡CH | S(O)OC$_2$H$_5$ | O | 2 | |
| CH$_2$—C≡CH | SO$_2$N(CH$_3$)(CH$_2$OCH$_3$) | O | 2 | |
| CH$_2$—C≡CH | C(=NOCH$_3$)NH$_2$ | O | 2 | |
| CH$_2$—C≡CH | C(=NOH)C$_6$H$_5$ | O | 2 | |
| CH(CH$_3$)C(CH$_3$)=CH$_2$ | CN | O | 2 | |
| CH(CH$_3$)C(CH$_3$)=CH$_2$ | SCN | O | 2 | |
| CH(CH$_3$)C(CH$_3$)=CH$_2$ | C(=NOCH$_3$)NH$_2$ | O | 2 | |
| CH(CH$_3$)C(CH$_3$)=CH$_2$ | C(=NOH)C$_6$H$_5$ | O | 2 | |
| CH(CH$_3$)C(CH$_3$)=CH$_2$ | SCCl$_2$F | O | 2 | |
| CH(CH$_3$)C(CH$_3$)=CH$_2$ | S(O)OCH$_3$ | O | 2 | |
| CH(CH$_3$)C(CH$_3$)=CH$_2$ | NH$_2$ | O | 2 | |
| CH(CH$_3$)C(CH$_3$)=CH$_2$ | SO$_2$N(CH$_3$)(CH$_2$OCH$_3$) | O | 2 | |
| C(CH$_3$)$_2$CH=CH$_2$ | SO$_2$OC$_2$H$_5$ | O | 2 | |
| C(CH$_3$)$_2$CH=CH$_2$ | CN | O | 2 | |
| C(CH$_3$)$_2$CH=CH$_2$ | SCN | O | 2 | |
| C(CH$_3$)$_2$CH=CH$_2$ | SCCl$_2$F | S | 2 | |
| C(CH$_3$)$_2$CH=CH$_2$ | NHCH$_3$ | O | 2 | |
| C(CH$_3$)$_2$CH=CH$_2$ | C(=NH)N(CH$_3$)$_2$ | O | 2 | |
| CH(CF$_3$)$_2$ | CN | O | 2 | |
| CH(CF$_3$)$_2$ | SCN | O | 2 | |
| CH(CF$_3$)$_2$ | NH$_2$ | O | 2 | |
| CH(CF$_3$)$_2$ | SCCl$_2$F | O | 2 | |
| CH(CF$_3$)$_2$ | S(O)OCH$_3$ | O | 2 | |

TABLE 1-continued

| R¹ | R² | Y | n | m.p.(°C.) |
|---|---|---|---|---|
| CH(CF₃)₂ | C(=NCH₃)NH₂ | O | 2 | |
| CH(CF₃)₂ | C(=NOCH₃)C₂H₅ | O | 2 | |
| CH(CF₃)₂ | SO₂N(CH₃)(CH₂OCH₃) | O | 2 | |
| CH₂—C≡C—CH₂Cl | SCN | O | 2 | |
| CH₂—C≡C—CH₂Cl | NH₂ | O | 2 | |
| CH₂—C≡C—CH₂Cl | SCCl₂F | O | 2 | |
| CH₂—C≡C—CH₂Cl | C(=NOH)NH₂ | O | 2 | |
| CH₂—C≡C—CH₂Cl | SO₂OCH₃ | O | 2 | |
| CH₂—C≡C—CH₂Cl | CN | O | 2 | |
| CH₂—C≡C—CH₂Cl | CN | S | 2 | |
| CH₂—C≡C—CH₂Cl | C(=NHNH₂)NH₂ | O | 2 | |
| CH₂—C≡C—CH₂Cl | Si(CH₃)₃ | O | 2 | |
| CH₂—CH=CH—CH₂Cl | CN | O | 2 | |
| CH₂—CH=CH—CH₂Cl | Si(CH₃)₃ | O | 2 | |
| CH₂—CH=CH—CH₂Cl | S(O)OC₂H₅ | O | 2 | |
| CH₂—CH=CH—CH₂Cl | SCCl₂F | O | 2 | |
| CH₂—CH=CH—CH₂Cl | NH₂ | O | 2 | |
| CH₂—CH=CH—CH₂Cl | C(=NOCH₃)NHCH₃ | O | 2 | |
| CH₂—CH=CH—CH₂Cl | SCN | O | 2 | |
| C(CH₃)₂C≡CH | CN | O | 2 | |
| C(CH₃)₂C≡CH | SCN | O | 2 | |
| C(CH₃)₂C≡CH | C(=NOCH₃)NH₂ | O | 2 | |
| C(CH₃)₂C≡CH | C(=NOH)C₂H₅ | O | 2 | |
| C(CH₃)₂C≡CH | SCCl₂F | O | 2 | |
| C(CH₃)₂C≡CH | SCH₃ | O | 2 | |
| C(CH₃)₂C≡CH | SO₂OCH₃ | O | 2 | |
| C(CH₃)₂C≡CH | SO₂N(CH₃)(CH₂OCH₃) | O | 2 | |
| CH₂CH₂OCH₃ | SCCl₂F | O | 2 | |
| CH₂CH₂OCH₃ | C(=NOCOCH₃)NH₂ | O | 2 | |
| CH₂CH₂OCH₃ | C(=NOH)C₆H₅ | O | 2 | |
| CH₂CH₂OCH₃ | SCN | O | 2 | |
| CH₂CH₂OCH₃ | S(O)OC₂H₅ | O | 2 | |
| CH₂CH₂OCH₃ | NH₂ | O | 2 | |
| CH₂CH₂OCH₃ | NHCH₃ | O | 2 | |
| CH₂CH₂OCH₃ | CN | S | 2 | |
| CH₂CH₂OCH₃ | CN | O | 1 | |
| CH(CH₂OCH₃)(C₂H₅) | CN | O | 2 | |
| CH(CH₂OCH₃)(C₂H₅) | SCN | O | 2 | |
| CH(CH₂OCH₃)(C₂H₅) | SCCl₂F | O | 2 | |
| CH(CH₂OCH₃)(C₂H₅) | SC₂H₅ | O | 2 | |
| CH(CH₂OCH₃)(C₂H₅) | S(O)OCH₃ | O | 2 | |
| CH(CH₂OCH₃)(C₂H₅) | C(=N—NH₂)NH₂ | O | 2 | |
| CH(CH₂OCH₃)(C₂H₅) | NH₂ | O | 2 | |
| CH₂CH₂SCH₃ | SCN | O | 2 | |
| CH₂CH₂SCH₃ | CN | O | 2 | |
| CH₂CH₂SCH₃ | SC₆H₄-p-Cl | O | 2 | |
| CH₂CH₂SCH₃ | S—CCl₂F | O | 2 | |
| CH₂CH₂SCH₃ | C(=NOCH₃)NH₂ | O | 2 | |
| CH₂CH₂SCH₃ | C(=NOH)C₂H₅ | O | 2 | |
| CH₂CH₂SCH₃ | N(CH₃)₂ | O | 2 | |
| CH₂CH₂SCH₃ | NH₂ | O | 2 | |
| CH₂CH₂SCH₃ | Si(CH₃)₃ | O | 2 | |
| CH(CH₂—SCH₃)(C₂H₅) | NH-i-C₃H₇ | O | 2 | |
| CH(CH₂—SCH₃)(C₂H₅) | SCCl₂F | O | 1 | |

TABLE 1-continued

| R¹ | R² | Y | n | m.p.(°C.) |
|---|---|---|---|---|
| CH(CH₂SCH₃)(C₂H₅) | C(=NOCH₃)NH₂ | O | 2 | |
| CH(CH₂SCH₃)(C₂H₅) | CN | O | 2 | |
| CH(CH₂SCH₃)(C₂H₅) | NH₂ | O | 2 | |
| CH(CH₂SCH₃)(C₂H₅) | SCN | O | 2 | |
| CH(CH₂SCH₃)(C₂H₅) | C(=NH)N(CH₃)₂ | O | 2 | |
| CH(CH₂SCH₃)(C₂H₅) | SO₂N(CH₃)(CH₂OCH₃) | O | 2 | |
| CH(CH₂SCH₃)(C₂H₅) | SCN | S | 2 | |
| C(CH₃)₂C(=O)CH₃ | CN | O | 2 | |
| C(CH₃)₂C(=O)CH₃ | SCN | O | 2 | |
| C(CH₃)₂C(=O)CH₃ | NH₂ | O | 2 | |
| C(CH₃)₂C(=O)CH₃ | SCCl₂F | O | 2 | |
| C(CH₃)₂C(=O)CH₃ | SCH₃ | O | 2 | |
| C(CH₃)₂C(=O)CH₃ | C(=NOCH₃)NH₂ | O | 2 | |
| CH(CH₃)C(=O)CH₃ | CN | O | 2 | |
| CH(CH₃)C(=O)CH₃ | S(O)OCH₃ | O | 2 | |
| CH(CH₃)C(=O)CH₃ | SO₂N(CH₃)(CH₂OCH₃) | O | 2 | |
| CH(CH₃)C(=O)CH₃ | C(=NOCH₃)NH₂ | O | 2 | |
| CH(CH₃)C(=O)CH₃ | C(=NH)N(CH₃)₂ | O | 2 | |
| CH(CH₃)C(=O)CH₃ | SCCL₂F | O | 2 | |
| CH(CH₃)C(=O)CH₃ | NH₂ | O | 2 | |
| CH(CH₃)C(=O)CH₃ | SCN | S | 2 | |

TABLE 1-continued

| R¹ | R² | Y | n | m.p.(°C.) |
|---|---|---|---|---|
| CH₂CH₂C(=O)CH₃ | N(CH₃)₂ | O | 2 | |
| CH₂CH₂C(=O)CH₃ | SCCl₂F | O | 2 | |
| CH₂CH₂C(=O)CH₃ | SCH₃ | O | 2 | |
| CH₂CH₂C(=O)CH₃ | NH₂ | O | 2 | |
| CH₂CH₂C(=O)CH₃ | SO₂N(CH₃)(CH₂OCH₃) | O | 2 | |
| CH₂CH₂C(=O)CH₃ | SCN | O | 2 | |
| CH₂CH₂C(=O)CH₃ | CN | O | 2 | |
| CH₂CO₂CH₃ | N(C₂H₅)₂ | O | 2 | |
| CH₂CO₂CH₃ | N(CH₃)(C₃H₇) | O | 2 | |
| CH₂CO₂CH₃ | CN | O | 2 | |
| CH₂CO₂CH₃ | SCN | O | 2 | |
| CH₂CO₂CH₃ | NH₂ | O | 1 | |
| CH₂CO₂CH₃ | S—C₆H₄-p-Cl | O | 2 | |
| CH₂CO₂CH₃ | C(=N—OC₂H₅)NH₂ | O | 2 | |
| CH₂CO₂CH₃ | C(=N—C₆H₁₁)NH₂ | O | 2 | |
| C(CH₃)(CH=CH₂)CO₂CH₃ | CN | O | 2 | |
| C(CH₃)(CH=CH₂)CO₂CH₃ | CN | O | 1 | |
| C(CH₃)(CH=CH₂)CO₂CH₃ | SCN | O | 2 | |
| C(CH₃)(CH=CH₂)CO₂CH₃ | C(=NOCH₃)NH₂ | O | 2 | |
| C(CH₃)(CH=CH₂)CO₂CH₃ | C(=NOCH₃)C₂H₅ | O | 2 | |
| C(CH₃)(CH=CH₂)CO₂CH₃ | SCCl₂F | O | 2 | |
| C(CH₃)(CH=CH₂)CO₂CH₃ | S(O)OCH₃ | O | 2 | |
| C(CH₃)(CH=CH₂)CO₂CH₃ | SO₂N(CH₃)(CH₂OCH₃) | O | 2 | |
| C(CH₃)(CH=CH₂)CO₂CH₃ | NH₂ | O | 2 | |
| CH₂C(=O)—NH—CH₃ | SCCl₂F | O | 2 | |

TABLE 1-continued

| R¹ | R² | Y | n | m.p.(°C.) |
|---|---|---|---|---|
| CH₂C(=O)—NH—CH₃ | C(=NOH)NH₂ | O | 2 | |
| CH₂C(=O)—NH—CH₃ | C(=NH)N(CH₃)₂ | O | 2 | |
| CH₂C(=O)—NH—CH₃ | N(CH₃)₂ | O | 2 | |
| CH₂C(=O)—NH—CH₃ | SO₂N(C₂H₅)(CH₂OC₂H₅) | O | 2 | |
| CH₂C(=O)—NH—CH₃ | CN | O | 2 | |
| CH₂C(=O)—NH—CH₃ | SCN | O | 2 | |
| CH₂C(=O)—N(CH₃)₂ | CN | O | 2 | |
| CH₂C(=O)—N(CH₃)₂ | SCCl₂F | O | 2 | |
| CH₂C(=O)—N(CH₃)₂ | SCH₃ | O | 2 | |
| CH₂C(=O)—N(CH₃)₂ | S(O)OCH₃ | S | 2 | |
| CH₂C(=O)—N(CH₃)₂ | NH-i-C₃H₇ | O | 2 | |
| CH₂C(=O)—N(CH₃)₂ | NH₂ | O | 2 | |
| CH₂C(=O)—N(CH₃)₂ | C(=NOH)NH₂ | O | 2 | |
| CH₂C(=O)—N(CH₃)₂ | Si(CH₃)₃ | O | 2 | |
| C₆H₅ | CN | O | 2 | 174–175 |
| C₆H₅ | SCN | O | 2 | |
| C₆H₅ | SCCl₂F | O | 2 | |
| C₆H₅ | NH₂ | O | 2 | |
| C₆H₅ | C(=NOH)NH₂ | O | 2 | |
| C₆H₅ | SO₂OCH₃ | O | 2 | |
| C₆H₅ | Si(CH₃)₃ | O | 2 | |
| C₆H₅ | CN | S | 2 | |

TABLE 1-continued

| R¹ | R² | Y | n | m.p.(°C.) |
|---|---|---|---|---|
| 2-CH₃-phenyl | CN | O | 2 | |
| 2-CH₃-phenyl | SCN | O | 2 | |
| 2-CH₃-phenyl | NH₂ | O | 2 | |
| 2-CH₃-phenyl | SCCl₂F | O | 2 | |
| 2-CH₃-phenyl | S(O)OCH₃ | O | 2 | |
| 2-F-phenyl | CN | O | 2 | |
| 2-F-phenyl | SCN | O | 2 | |
| 2-F-phenyl | SCH₃ | O | 2 | |
| 2-F-phenyl | SO₂OCH₃ | O | 2 | |
| 2-F-phenyl | N(CH₃)₂ | O | 2 | |
| 2-F-phenyl | NH₂ | O | 1 | |

TABLE 1-continued

| R¹ | R² | Y | n | m.p.(°C.) |
|---|---|---|---|---|
| 3-F-C₆H₄- | CN | O | 2 | |
| 3-F-C₆H₄- | NH₂ | O | 2 | |
| 3-F-C₆H₄- | SCN | O | 2 | |
| 3-F-C₆H₄- | C(=NOCH₃)C₂H₅ | O | 2 | |
| 3-F-C₆H₄- | CN | O | 2 | |
| 4-F-C₆H₄- | CN | S | 2 | |
| C₆H₅-F | CN | O | 2 | |
| 4-CH₃-C₆H₄- | CN | O | 2 | |
| N-pyrrolyl | CN | O | 2 | |

TABLE 2

| X | Ring position | m | R¹ | R² | Y | n | m.p.(°C.) |
|---|---|---|---|---|---|---|---|
| CH₃ | 5,6,7 | 1 | CH₃ | CN | O | 2 | |
| CH₃ | 5,6,7,8 | 1 | C₂H₅ | CN | O | 2 | |
| CH₃ | 5,6,7,8 | 1 | n-C₃H₇ | CN | O | 2 | |
| CH₃ | 8 | 1 | i-C₃H₇ | CN | O | 2 | 103–104 |
| CH₃ | 8 | 1 | i-C₃H₇ | SCN | O | 2 | |
| CH₃ | 8 | 1 | i-C₃H₇ | NH₂ | O | 2 | |
| CH₃ | 8 | 1 | i-C₃H₇ | C(=NOH)NH₂ | O | 2 | |
| CH₃ | 8 | 1 | i-C₃H₇ | SCCl₂F | O | 2 | |
| CH₃ | 8 | 1 | i-C₃H₇ | S(O)OCH₃ | O | 2 | |
| CH₃ | 8 | 1 | i-C₃H₇ | Si(CH₃)₃ | O | 2 | |
| CH₃ | 6,8 | 2 | i-C₃H₇ | CN | O | 2 | |
| Br | 6 | 1 | i-C₃H₇ | CN | O | 2 | 76–77 |
| Br | 5,7,8 | 1 | i-C₃H₇ | CN | O | 2 | |
| Br | 6,8 | 2 | i-C₃H₇ | CN | O | 2 | 119–120 |
| Br | 6 | 1 | sec C₄H₉ | CN | O | 2 | |
| Br | 6 | 1 | sec C₄H₉ | CN | S | 2 | |
| Cl | 5,6 | 1 | i-C₃H₇ | CN | O | 2 | |
| Cl | 7 | 1 | i-C₃H₇ | CN | O | 2 | 146–147 |
| Cl | 7 | 1 | i-C₃H₇ | NH₂ | O | 2 | |
| Cl | 7 | 1 | i-C₃H₇ | SCN | O | 2 | |
| Cl | 7 | 1 | i-C₃H₇ | SCCl₂F | O | 2 | |
| Cl | 7 | 1 | i-C₃H₇ | N(CH₃)₂ | O | 2 | |
| Cl | 7 | 1 | sec C₄H₉ | CN | O | 2 | |
| Cl | 8 | 1 | i-C₃H₇ | CN | O | 2 | 123–124 |
| Cl | 8 | 1 | i-C₃H₇ | SCN | O | 2 | |
| Cl | 8 | 1 | i-C₃H₇ | NH₂ | O | 2 | |
| Cl | 8 | 1 | i-C₃H₇ | n(CH₃)₂ | O | 2 | |

TABLE 2-continued

| X | Ring position | m | R¹ | R² | Y | n | m.p.(°C.) |
|---|---|---|---|---|---|---|---|
| Cl | 8 | 1 | i-C$_3$H$_7$ | SCH$_3$ | O | 2 | |
| Cl | 8 | 1 | i-C$_3$H$_7$ | SCCl$_2$F | S | 2 | |
| Cl | 8 | 1 | i-C$_3$H$_7$ | S(O)OCH$_3$ | O | 2 | |
| Cl | 8 | 1 | i-C$_3$H$_7$ | Si(CH$_3$)$_3$ | O | 2 | |
| Cl | 5,6,7,8 | 1 | n-C$_3$H$_7$ | CN | O | 2 | |
| F | 5,6,7 | 1 | i-C$_3$H$_7$ | CN | O | 2 | |
| F | 5,6,7,8 | 4 | i-C$_3$H$_7$ | CN | O | 2 | |
| CH$_3$, Cl | 6, 8 | 2 | i-C$_3$H$_7$ | CN | O | 2 | |
| ◁ | 8 | 1 | i-C$_3$H$_7$ | CN | O | 2 | |
| ⬡ (phenyl) | 5,6,7,8 | 1 | i-C$_3$H$_7$ | CN | O | 2 | |
| ClCH$_2$ | 5,6,7,8 | 1 | i-C$_3$H$_7$ | CN | O | 2 | |
| NO$_2$ | 5,6,7,8 | 1 | i-C$_3$H$_7$ | CN | O | 2 | |
| NO$_2$ | 5,6,7,8 | 1 | i-C$_3$H$_7$ | CN | O | 1 | |
| F | 8 | 1 | i-C$_3$H$_7$ | CN | O | 2 | 89–91 |
| NO$_2$ | 5,6,7,8 | 1 | i-C$_3$H$_7$ | CN | O | 2 | |
| NO$_2$ | 6,8 | 2 | i-C$_3$H$_7$ | CN | O | 2 | |
| CH$_3$, NO$_2$ | 6,8 | 2 | i-C$_3$H$_7$ | CN | O | 2 | |
| NH$_2$ | 5,6,7,8 | 1 | i-C$_3$H$_7$ | CN | O | 2 | |
| CH$_3$, NO$_2$ | 6,8 | 2 | sec C$_4$H$_9$ | CN | O | 2 | |
| SCN | 5,6,7,8 | 1 | C$_2$H$_5$ | CN | O | 2 | |
| SCN | 5,6,7,8 | 1 | n-C$_3$H$_7$ | CN | O | 2 | |
| SCN | 5,6,7,8 | 1 | i-C$_3$H$_7$ | CN | O | 2 | |
| SCN | 5,6,7,8 | 1 | ⬡H (cyclohexyl) | CN | O | 2 | |
| CO$_2$CH$_3$ | 5,6,8 | 1 | i-C$_3$H$_7$ | CN | O | 2 | |
| CO$_2$CH$_3$ | 7 | 1 | i-C$_3$H$_7$ | CN | O | 2 | 126–127 |
| CO$_2$CH$_3$ | 5,6,7,8 | 1 | sec C$_4$H$_9$ | CN | O | 2 | |
| CO$_2$CH$_3$ | 5,6,7,8 | 1 | i-C$_3$H$_7$ | CN | S | 2 | |
| N(CH$_3$)$_2$ | 5,6,7,8 | 1 | i-C$_3$H$_7$ | CN | O | 2 | |
| N(CH$_3$)$_2$ | 5,6,7,8 | 1 | n-C$_3$H$_7$ | CN | O | 2 | |
| OCH$_3$ | 5,6,7,8 | 1 | i-C$_3$H$_7$ | CN | O | 2 | |
| OCH$_3$ | 5,6,7,8 | 1 | sec C$_4$H$_9$ | SCN | O | 2 | |
| OCH$_3$ | 5,6,7,8 | 1 | i-C$_3$H$_7$ | N(CH$_3$)$_2$ | O | 2 | |
| SCH$_3$ | 5,6,7,8 | 1 | i-C$_3$H$_7$ | CN | O | 2 | |
| SCH$_3$ | 5,6,7,8 | 1 | i-C$_3$H$_7$ | SCN | O | 2 | |
| SO$_2$CH$_3$ | 5,6,7,8 | 1 | CH$_3$ | CN | O | 2 | |
| SO$_2$CH$_3$ | 5,6,7,8 | 1 | i-C$_3$H$_7$ | CN | O | 2 | |
| SO$_2$CH$_3$ | 5,6,7,8 | 1 | sec C$_4$H$_9$ | CN | O | 2 | |
| SO$_2$OCH$_3$ | 5,6,7,8 | 1 | i-C$_3$H$_7$ | CN | O | 2 | |
| SO$_2$OCH$_3$ | 5,6,7,8 | 1 | i-C$_3$H$_7$ | N(CH$_3$)$_2$ | O | 2 | |
| SO$_2$OCH$_3$ | 5,6,7,8 | 1 | i-C$_3$H$_7$ | NH$_2$ | O | 1 | |
| SO$_2$OCH$_3$ | 5,6,7,8 | 1 | i-C$_3$H$_7$ | CN | O | 2 | |
| SO$_2$N(CH$_3$)$_2$ | 5,6,7,8 | 1 | i-C$_3$H$_7$ | SCN | O | 2 | |
| CCl$_3$ | 5,6,7,8 | 1 | i-C$_3$H$_7$ | CN | O | 2 | |
| CCl$_3$ | 5,6,7,8 | 1 | sec C$_4$H$_9$ | CN | O | 2 | |
| CF$_3$ | 5,6,7,8 | 1 | i-C$_3$H$_7$ | CN | O | 2 | |
| CF$_3$ | 5,6,7,8 | 1 | i-C$_3$H$_7$ | SCN | O | 2 | |
| CF$_3$ | 5,6,7,8 | 1 | i-C$_3$H$_7$ | N(CH$_3$)$_2$ | O | 2 | |
| C(O)CH$_3$ | 5,6,7,8 | 1 | i-C$_3$H$_7$ | CN | O | 2 | |
| C(O)H | 5,6,7,8 | 1 | i-C$_3$H$_7$ | CN | O | 2 | |
| OH | 5,6,7,8 | 1 | i-C$_3$H$_7$ | CN | O | 2 | |
| SH | 5,6,7,8 | 1 | i-C$_3$H$_7$ | CN | O | 2 | |
| SO$_2$NHCH$_3$ | 5,6,7,8 | 1 | i-C$_3$H$_7$ | CN | O | 2 | |
| SO$_2$NHC$_2$H$_5$ | 5,6,7,8 | 1 | i-C$_3$H$_7$ | SCN | O | 2 | |
| OCF$_2$CF$_3$ | 5,6,7,8 | 1 | i-C$_3$H$_7$ | CN | O | 2 | |
| OCF$_2$CF$_3$ | 5,6,7,8 | 1 | sec C$_4$H$_9$ | CN | O | 2 | |
| OCF$_2$CH$_3$ | 5,6,7,8 | 1 | i-C$_3$H$_7$ | CN | O | 2 | |
| OCF$_2$CCl$_3$ | 5,6,7,8 | 1 | i-C$_3$H$_7$ | CN | O | 2 | |
| Cl | 5,6,7,8 | 1 | C$_6$H$_5$ | CN | O | 2 | |

TABLE 2-continued

| X | Ring position | m | R¹ | R² | Y | n | m.p.(°C.) |
|---|---|---|---|---|---|---|---|
| Cl | 5,6,7,8 | 1 | 2-fluorophenyl | CN | O | 2 | |
| Cl | 5,6,7,8 | 1 | 4-fluorophenyl | CN | O | 2 | |
| Cl | 5,6,7,8 | 1 | 3-fluorophenyl | CN | O | 2 | |
| Cl | 5,6,7,8 | 1 | 3-fluorophenyl | CN | S | 2 | |
| $CH_3$ | 5,6,7,8 | 1 | $C_6H_5$ | CN | O | 2 | |
| $CH_3$ | 5,6,7,8 | 1 | 3-fluorophenyl | CN | O | 2 | |
| $CH_3$ | 5,6,7,8 | 1 | cyclopropyl | CN | O | 2 | |
| Cl | 5,6,7,8 | 1 | cyclopropyl | CN | O | 2 | |
| $CH_3$ | 5,6,7,8 | 1 | $CH_2CH=CH_2$ | CN | O | 2 | |
| $CH_3$ | 5,6,7,8 | 1 | $C(CH_3)_3$ | CN | O | 2 | |
| Cl | 5,6,7,8 | 1 | $CH_2CH=CH_2$ | CN | O | 2 | |
| $CH_3$ | 5,6,7,8 | 1 | $CH(CH_3)CH=CH_2$ | CN | O | 2 | |
| $CH_3$ | 5,6,7,8 | 1 | $CH(CH_3)CH=CH_2$ | SCN | O | 2 | |
| Cl | 5,6,7,8 | 1 | $CH(CH_3)CH\equiv CH_2$ | CN | O | 2 | |
| $CH_3$ | 5,6,7,8 | 1 | $CH(CH_3)C\equiv CH$ | CN | O | 2 | |
| Cl | 5,6,7,8 | 1 | $CH(CH_3)C\equiv CH$ | CN | O | 2 | |
| $CH_3$ | 5,6,7,8 | 1 | $CH_2-C(CH_3)=CH_2$ | CN | O | 2 | |
| $CH_3$ | 5,6,7,8 | 1 | $CH(CH_3)CH_2OCH_3$ | CN | O | 2 | |
| $CH_3$ | 5,6,7,8 | 1 | $CH(CH_3)CH_2OCH_3$ | CN | S | 2 | |
| $CH_3$ | 5,6,7,8 | 1 | $CH(CH_3)CH_2OCH_3$ | CN | O | 1 | |
| Br(6), $CH_3$(8) | 6,8 | 2 | i-$C_3H_7$ | CN | O | 2 | |

Experiments for determining the herbicidal action of the new 2,1,3-benzothiadiazine compounds The herbicidal and selective properties of the new compounds were investigated in greenhouse and field experiments.

EXAMPLE 7

(greenhouse experiments)

Plastic flowerpots having a volume of 300 cm³ were filled with a sandy loam. Seeds were then sown, pregerminated tubers (e.g. Cyperus esculentus) planted or vegetatively reproduced species transplanted. The test plants were separated according to species. Only seeds were used for the preemergence treatment. The active ingredients were suspended or emulsified in water as the vehicle and sprayed onto the surface of the soil by means of atomizing nozzles. After treatment, the vessels were lightly sprinkler-irrigated and then covered with transparent plastic hoods until the plants had taken root. For the postemergence (leaf) treatment, the plants were first grown to a height of from 3 to 10 cm, depending on habit, before being treated. The pots were of course not irrigated, and no hoods were placed on the pots. The plants were placed in either cooler or warmer parts of the greenhouse, depending on their temperature requirements. The experiments were run for from 2 to 4 weeks. During this period the plants were tended and their reaction to the individual treatments was assessed. The application rate of the compounds examined is given in kg/ha of active ingredient. For assessment, the 0 to 100 scale was used, 0 denoting no damage or normal emergence, and 100 denoting no emergence or complete destruction.

EXAMPLE 8

(experiments in the open)

Postemergence treatments were carried out on small plots. The compounds were applied, as an emulsion or suspension in water, with the aid of a motor-driven plot spray mounted on a hitch. All the experiments were observed for several weeks and again assessed on the 0 to 100 scale.

Results

The following statements may be made with regard to the new compounds:

1. The action of the compounds when applied to the soil (preemergence) was approximately equivalent to that of the comparative agent. A shift in action was indicated (Table 2).

2. The introduction of the cyano group in the 1-position in the 2,1,3-benzothiadiazin-(4)-one-2,2-dioxides resulted in a surprising increase in action and in an extension of the spectrum of combattable unwanted plant species (Tables 3, 4, 5, 6, 7 and 8). An additional feature is the increased reliability of the new compounds.

3. The new compounds are well tolerated by numerous crop plants (Tables 3, 4, 5, 6, 7 and 8).

The compounds according to the invention are therefore of outstanding value as selective herbicides, and represent a considerable enrichment of the art.

Table 1

| | List of plant names | |
|---|---|---|
| Botanical name | Abbreviation in tables | Common name |
| Abutilon theophrastii | Abut. theo. | velvet leaf |
| Anthemis spp. | Anth. | chamomile |
| Arachys hypogaea | Arachys hyp. | peanuts (groundnuts) |
| Bidens pilosa | Bidens pil. | |
| Chenopodium album | Chen. alb. | lambsquarters |
| Cyperus difformis | Cyp. diff. | smallflower umbrellaplant |
| Cyperus esculentus | Cyper. escul. | yellow nutsedge |
| Cyperus ferax | Cyper. ferox | |
| Daucus carota | — | carrot |
| Galinsoga spp. | Galins. spp. | gallant soldier |
| Galium aparine | Galium apar. | catchweed bedstraw |
| Glycine max | Glyc. max | soybeans |
| Lamium spp. | Lam. spp. | dead-nettle (henbit) |
| Ludwigia prostrata | Ludw. pros. | |
| Matricaria spp. | Matric. spp. | chamomile |
| Medicago sativa | Medi. sat. | alfalfa |
| Mercurialis annua | Mercur. annua | annual mercury |
| Oryza sativa | Oryza sat. | rice |
| Phaseolus vulgaris | Phaseo. vulg. | snapbean |
| Portulaca oleracea | Port. oler. | common purslane |
| Sesbania exaltata | Sesb. exal. | hemp sesbania (coffeeweed) |
| Sida spinosa | Sida spin. | teaweed (prickly sida) |
| Sinapis alba | — | white mustard |
| Sinapis arvensis | Sinap. arv. | yellow charlock |
| Sorghum bicolor | Sorgh. bic. | sorghum |
| Solanum nigrum | Sol. nig. | black nightshade |
| Stellaria media | Stellaria media | chickweed |
| Triticum aestivum | Triti. aest. | wheat |
| Zea mays | — | Indian corn |
| Centaurea cyanus | — | cornflower |

Table 2

Preemergence application in the greenhouse

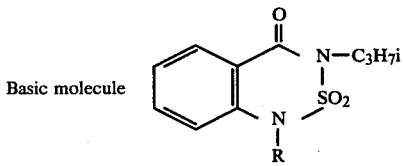

Basic molecule

| Compound no. | Substituents R | Appl. rate ka/ha | Test plants and % damage | | |
|---|---|---|---|---|---|
| | | | Daucus carota | Sida spinosa | Sinapis alba |
| 1 | CN | 1.0 | 90 | 55 | 80 |
| | | 2.0 | 90 | 78 | 80 |
| 2 prior art (German 1 542 836) | H | 1.0 | 100 | 70 | 40 |
| | | 2.0 | 100 | 90 | 80 |

0 = no damage
100 = complete destruction

Table 3

| Compound no. | Appl. rate kg/ha | Areas of action and application; postemergenece treatment in the greenhouse | | | | | | | | | | | |
|---|---|---|---|---|---|---|---|---|---|---|---|---|---|
| | | Test plants and % damage | | | | | | | | | | | |
| | | Glyc. max | Medi. sat. | Phaseo. vulg. | Sorgh. bic. | Abut. thoe. | Cyp. diff. | Chen. alb. | Lamium spp. | Merc. ann. | Port. oler. | Sesb. exalt. | Stell. med. |
| 1 | 1,0 | 0 | 0 | 0 | 0 | 99 | 47 | 50 | 100 | 100 | 100 | 60 | 100 |
|   | 2,0 | 0 | 0 | 10 | 0 | 99 | 60 | 85 | 100 | 100 | 100 | 80 | 100 |
|   | 4,0 | 3 | 0 | 10 | 0 | — | 68 | — | — | — | — | — | — |
| 2 | 1,0 | 0 | 0 | 0 | 0 | 99 | 53 | 65 | 50 | 30 | 100 | 50 | 95 |
|   | 2,0 | 0 | 0 | 0 | 0 | 99 | 67 | 65 | 50 | 60 | 100 | 60 | 95 |
|   | 4,0 | 0 | 20 | 0 | 0 | — | 70 | — | — | — | — | — | — |

0 = no damage
100 = complete destruction

Table 4

| Compound no. | Appl. rate kg/ha | Removal of unwanted plants from soybeans and Indian corn; postemergence treatment in the open | | | | | | | | |
|---|---|---|---|---|---|---|---|---|---|---|
| | | Test plants and % damage | | | | | | | | |
| | | Glycine max | | | Zea mays | Anth./ Matr. | Galins. spp. | Lamium spp. | Stell. med. | Sinap. arv. |
| | | cv. Bragg | cv. Dare | cv. SRF 450 | | | | | | |
| 1. | 0,5 | 0 | 2 kg/ha | 0 | 0 | 80 | 82 | 45 | 91 | 100 |
|    | 1,0 | 0 | 0 | 2 | 0 | 96 | 96 | 70 | 99 | 100 |
|    | 4,0 | 2,5 | | 11 | — | 100 | 100 | 100 | 100 | 100 |
| 2. | 0,5 | 0 | — | 0 | 0 | 94 | 71 | 17 | 92 | 100 |
|    | 1,0 | 0 | 12 | 4 | 0 | 100 | 88 | 53 | 98 | 100 |
|    | 4,0 | 17 | — | 14 | — | 100 | 100 | 100 | 100 | 100 |

0 = no damage
100 = complete destruction

Table 5

Herbicidal action after postemergence application in the greenhouse

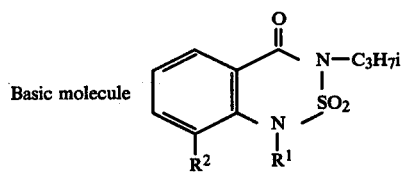

Basic molecule

| Substituents | | Appl. rate kg/ha | Test plants and % damage | | | | | | |
|---|---|---|---|---|---|---|---|---|---|
| R$^1$ | R$^2$ | | Tritic. aest. | Chenop. album | Cyper. escul. | Matr. spp. | Merc. annua | Sinapis arv. | Stell. med. |
| CH$_3$ prior art (German Laid-Open Application DOS 2,443,901) | CH$_3$ | 2.0 | 0 | 0 | 0 | 0 | 0 | 0 | 0 |
| CN | CH$_3$ | 1.0 | 0 | 100 | 0 | 100 | 100 | 100 | 100 |
| CN | Cl | 1.0 | 0 | 100 | 65 | 100 | 100 | 100 | 100 |

0 = no damage
100 = complete destruction

Table 6

Herbicidal action after postemergence application in the greenhouse

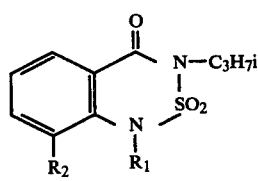

| Substituents | | | Test plants and % damage | | | | | | | | | |
|---|---|---|---|---|---|---|---|---|---|---|---|---|
| R$_1$ | R$_2$ | kg/ha | Glyc. max | Triti. aest. | Zea mays | Cyper. esc. | Galium apar. | Lam. spp. | Ludw. pros. | Sida spin. | Sesb. exal. | Sol. nig. |
| CN | Cl | 0.25 | — | — | 0 | — | 50 | — | 78 | 86 | 100 | 100 |
|    |    | 1.0 | 0 | 3 | 0 | 68 | 78 | 73 | 95 | 100 | 100 | 100 |
|    |    | 2.0 | 6 | 7 | 5 | 78 | 95 | 72 | — | 100 | 100 | 100 |
| H  | Cl | 0.25 | — | — | — | — | 36 | — | 65 | 55 | 90 | 86 |

Table 6-continued
Herbicidal action after postemergence application in the greenhouse

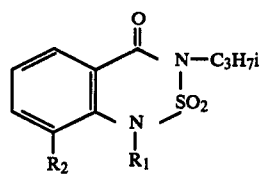

| Substituents | | | Test plants and % damage | | | | | | | | | |
|---|---|---|---|---|---|---|---|---|---|---|---|---|
| | | | Glyc. | Triti. | Zea | Cyper. | Galium | Lam. | Ludw. | Sida | Sesb. | Sol. |
| $R_1$ | $R_2$ | kg/ha | max | aest. | mays | esc. | apar. | spp. | pros. | spin. | exal. | nig. |
| prior art | | 1.0 | 0 | 2 | 0 | 36 | 63 | 20 | 95 | 98 | 100 | 100 |
| (German Laid-Open Application DOS 2,443,901) | | 2.0 | 0 | 2 | 0 | 41 | 71 | 30 | — | 98 | 100 | 100 |

0 = no damage
100 = complete destruction

Table 7
Herbicidal action of the new compounds

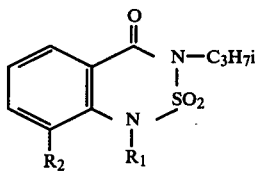

| Substituents | | | Test plants and % damage | | | | | | | | |
|---|---|---|---|---|---|---|---|---|---|---|---|
| | | | Arachys | Glyc. | Oryza | Triti. | Abut. | Bidens | Cyper. | Mercur. | Sol. |
| $R_1$ | $R_2$ | kg/ha | hyp. | max | sat. | aest. | theo. | pil. | ferax | annua | nig. |
| CN | F | 0.25 | — | 0 | — | 0 | 100 | 100 | 95 | 99 | 100 |
| | | 1.0 | 10 | 0 | 15 | 0 | 100 | 100 | 100 | 99 | 100 |
| H | H | 0.25 | — | 0 | — | 2 | 69 | 63 | 50 | 42 | 93 |
| prior art | | 1.0 | 0 | 0 | 5 | 2 | 87 | 90 | 80 | 65 | 100 |

0 = no damage
100 = complete destruction

Table 8
Herbicidal action of the new compounds; postemergence application in the open Basic molecule 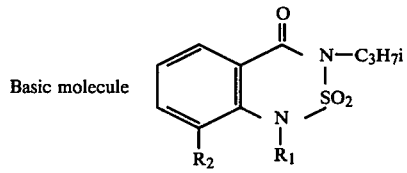

| Substituents | | | Test plants and % damage | | | |
|---|---|---|---|---|---|---|
| | | | Triti. | Galium | Matric. | Stellaria |
| $R_1$ | $R_2$ | kg/ha | aest. | apar. | spp. | media |
| CN | H | 0.5 | 0 | 45 | 100 | 95 |
| | | 1.0 | 0 | 68 | 100 | 98 |
| | | 1.5 | 0 | 95 | 100 | 100 |
| CN | $CH_3$ | 0.5 | 0 | 65 | 100 | 95 |
| | | 1.0 | 0 | 85 | 100 | 100 |
| | | 1.5 | 0 | 92 | 100 | 100 |
| H prior art | H | 0.5 | 0 | 10 | 100 | 65 |
| | | 1.0 | 0 | 30 | 100 | 85 |

Table 8-continued
Herbicidal action of the new compounds; postemergence application in the open Basic molecule 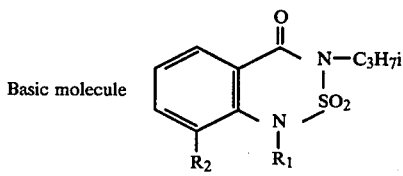

| Substituents | | | Test plants and % damage | | | |
|---|---|---|---|---|---|---|
| | | | Triti. | Galium | Matric. | Stellaria |
| $R_1$ | $R_2$ | kg/ha | aest. | apar. | spp. | media |
| (German 1,542,836) | | 1.5 | 0 | 70 | 100 | 98 |
| H prior art | $CH_3$ | 0.5 | 0 | 12 | 95 | 45 |
| | | 1.0 | 0 | 30 | 100 | 65 |
| (German 2,443,901) | | 1.5 | 0 | 50 | 100 | 75 |

0 = no damage
100 = complete destruction

Table 9

Herbicidal action of the new compounds in *Sinapis alba* and *Centaurea cyanus*; postemergence application in the greenhouse Basic molecule:

[Structure: benzene ring with X substituent, C(=O)-N(R$_2$)-SO$_2$-N(R$_1$) group]

| Substituents R$_1$ | R$_2$ | X | Ring substitution | kg/ha | *Sinapis alba* % damage |
|---|---|---|---|---|---|
| CN | CH$_3$ | H | — | 2,0 | 100 |
| CN | C$_2$H$_5$ | H | — | 2,0 | 100 |
| CN | C$_4$H$_9$sec | H | — | 2,0 | 85 |
| CN | cyclopropyl | H | — | 2,0 | 90 |
| CN | C$_3$H$_7$i | Cl | 7 | 2,0 | 100 |
| CN | C$_3$H$_7$i | Br$_2$ | 6,8 | 2,0 | 80 |
| C=N—OCH$_3$ / NH$_2$ | C$_3$H$_7$i | H | — | 2,0 | 100 |
| SO$_2$N(C$_2$H$_5$)(CH$_2$OCH$_3$) | C$_3$H$_7$i | H | — | 2,0 | 100 |

| | | | | | *Centaurea cyanus* |
|---|---|---|---|---|---|
| SCCl$_2$F | C$_2$H$_5$ | H | — | 2,0 | 100 |
| CN | C$_3$H$_7$i | Br$_2$CH$_3$ | 6,8 | 3,0 | 100 |

0 = no damage
100 = complete destruction

Suitable application methods for the new active ingredients are soil incorporation, treatment of the soil surface, and particularly postemergence treatment. Special applications such as post-directed or lay-by treatment are also possible. In this case, the spray is directed in such a manner that the leaves of sensitive crop plants are not touched; the agents are sprayed onto the soil beneath the crop plants, or the unwanted plants growing there.

In view of the wide variety of application methods, the agents according to the invention, or compositions containing them, may be used not only in the crop plants in the above tables, but also in a further large number of crop plants for eliminating unwanted plants. The application rates may vary from 0.1 to 15 kg/ha and more.

The following crop plants may be mentioned by way of example:

| Botanical Name | Common name |
|---|---|
| *Allium cepa* | onion |
| *Ananas comosus* | pineapple |
| *Asparagus officinalis* | asparagus |
| *Avena sativa* | oats |
| *Beta vulgaris* spp. *altissima* | sugarbeet |
| *Beta vulgaris* spp. *rapa* | fodder beet |
| *Beta vulgaris* spp. *esculenta* | table beet, red beet |
| *Brassica napus* var. *napus* | rape |
| *Brassica napus* var. *napobrassica* | |
| *Brassica napus* va. *rapa* | turnip |
| *Brassica rapa* var. *silvestris* | |
| *Camellia sinensis* | tea plant |
| *Carthamus tinctorius* | safflower |
| *Citrus limon* | lemon |
| *Citrus maxima* | grapefruit |
| *Citrus reticulata* | |
| *Citrus sinensis* | orange |
| *Coffea arabica* (*Coffea canaphora,* | |
| *Coffea liberica*) | coffee |
| *Cucumis melo* | melon |
| *Cucumis sativus* | cucumber |
| *Cynodon dactylon* | Bermudagrass in turf and lawns |
| *Elaeis guineensis* | oil palm |
| *Fragaria vesca* | strawberry |
| *Gossypium hirsutum* | |
| (*Gossypium arboreum* | |
| *Gossypium herbaceum* | cotton |
| *Gossypium vitifolium*) | |
| *Helianthus annuus* | sunflower |
| *Helianthus tuberosus* | |
| *Hevea brasiliensis* | rubber plant |
| *Hordeum vulgare* | barley |
| *Humulus lupulus* | hops |
| *Ipomoea batatas* | sweet potato |
| *Lactuca sativa* | lettuce |
| *Lens culinaris* | lentil |
| *Linum usitatissimum* | flax |
| *Lycopersicon lycopersicum* | tomato |
| *Malus*spp. | apple |
| *Manihot esculenta* | cassava |
| *Mentha piperita* | peppermint |
| *Musa*spp. | banana |
| *Nicotiana tabacum* (*N. rustica*) | tobacco |
| *Olea europaea* | olive |
| *Panicum miliaceum* | |
| *Phaseolus lunatus* | limabean |
| *Phaseolus mungo* | mungbean |
| *Pennisetum glaucum* | |
| *Petroselinum crispum* spp.*tuberosum* | parsley |
| *Picea abies* | Norway spruce |
| *Abies alba* | fir |
| *Pinus* spp. | pine |
| *Pisum sativum* | English pea |
| *Prunus avium* | cherry |
| *Prunus domestica* | plum |
| *Prunus persica* | peach |

-continued

| Botanical Name | Common name |
|---|---|
| *Pyrus communis* | pear |
| *Ribes sylvestre* | red currant |
| *Ribes uva-crispa* | |
| *Ricinus communis* | |
| *Saccharum officinarum* | sugar cane |
| *Secale cereale* | rye |
| *Sesamum indicum* | Sesame |
| *Solanum tuberosum* | Irish potato |
| *Sorghum dochna* | |
| *Spinacia oleracea* | spinach |
| *Theobroma cacao* | cacao |
| *Trifolium pratense* | red clover |
| *Vaccinium corymbosum* | blueberry |
| *Vaccinium vitis-idaea* | cranberry |

-continued

| Botanical Name | Common name |
|---|---|
| *Vicia faba* | tick bean |
| *Vigna sinensis (V. unguiculata)* | cow pea |
| *Vitis vinifera* | grape |

To extend the spectrum of action of the new individual active ingredients, to achieve synergistic effects or to improve persistence in the soil, numerous other herbicidal and growth-regulating compounds may be used as components in compositions and combinations. Depending on the intended area of use and the envisaged objective, the following compounds or similar derivatives may be used:

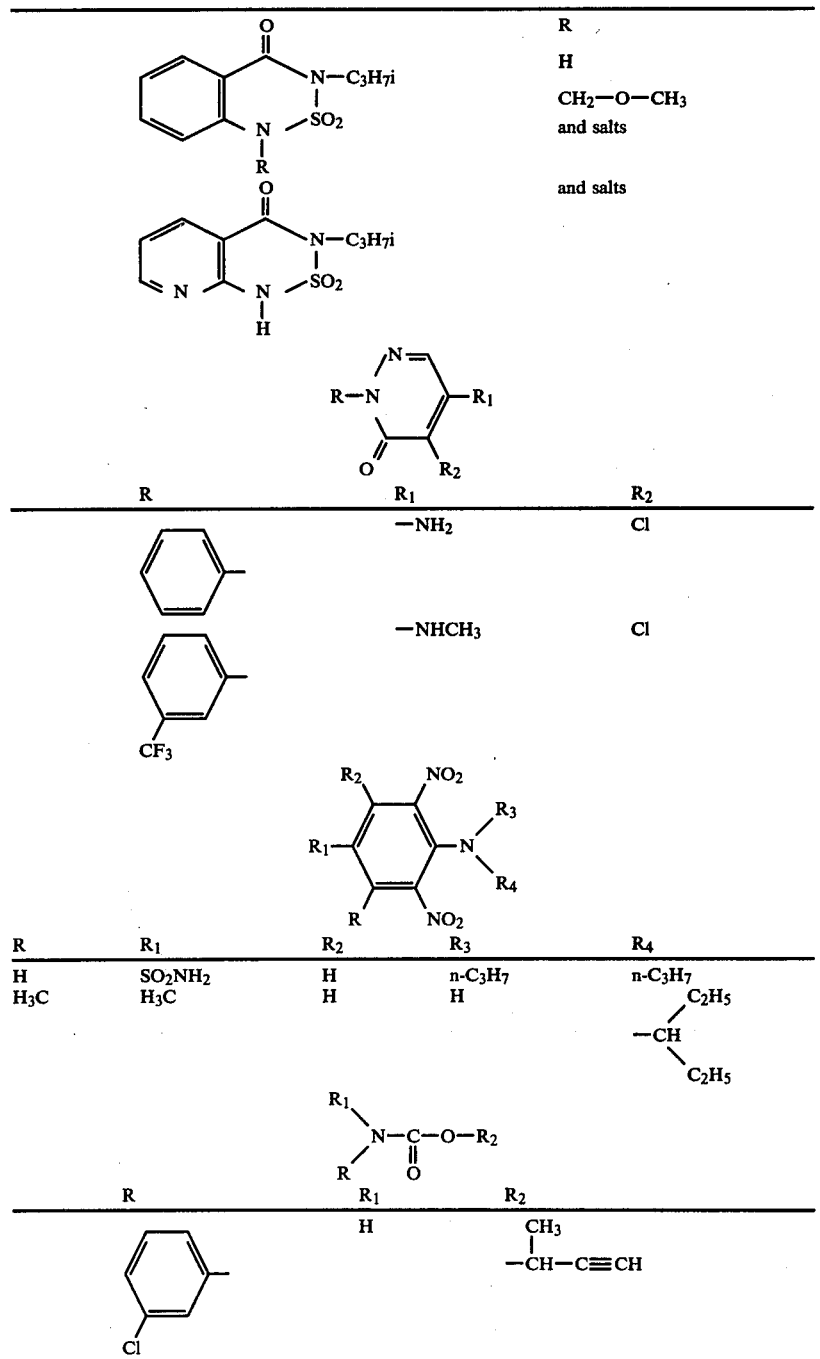

-continued
| | | |
|---|---|---|
| 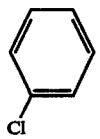 | H | —CH$_2$—C≡C—CH$_2$Cl |
| 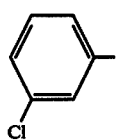 | H | i-C$_3$H$_7$ |
| 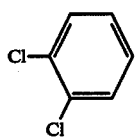 | H | CH$_3$ |
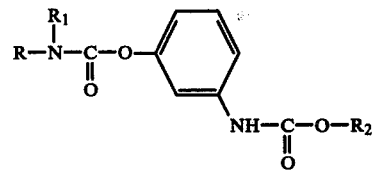
| R | R$_1$ | R$_2$ |
|---|---|---|
| 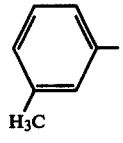 | H | CH$_3$ |
| 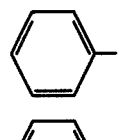 | H | C$_2$H$_5$ |
| 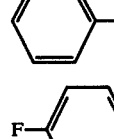 | CH$_3$ | CH$_3$ |
|  | H | CH$_3$ |
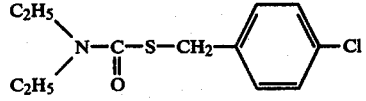
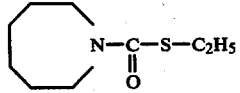
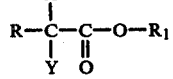
| R | X | Y | R$_1$ |
|---|---|---|---|
| CH$_3$ | Cl | Cl | Na |
| | Cl | H | CH$_3$ |
| 4-Cl-C$_6$H$_4$-CH$_2$ | | | |
| C$_6$H$_5$-C(O)-N(H)-O— | H | H | H salts |

-continued
| | | | |
|---|---|---|---|
| 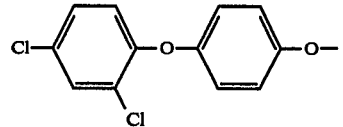 | H | CH₃ | CH₃ |
| 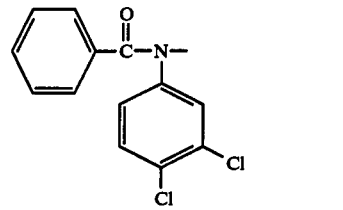 | H | CH₃ | C₂H₅ |
| 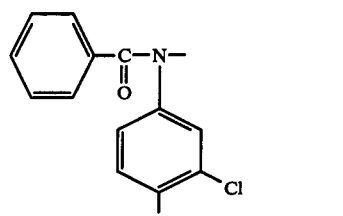 | H | CH₃ | i-C₃H₇ |
| 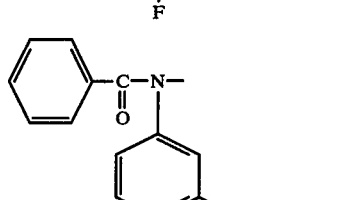 | H | CH₃ | CH₃ |
| 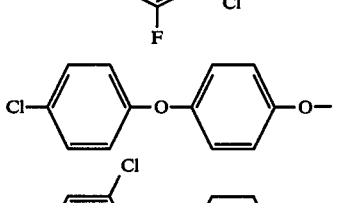 | H | CH₃ | —CH₂—CH(CH₃)CH₃ |
| 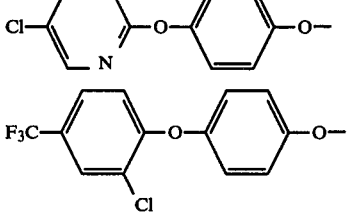 | H | CH₃ | Na |
|  | H | CH₃ | Na |
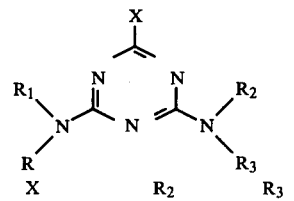
| R | R₁ | X | R₂ | R₃ |
|---|---|---|---|---|
| H | tert.-C₄H₉ | SCH₃ | H | C₂H₅ |
| H | i-C₃H₇ | SCH₃ | H | i-C₃H₇ |
| H | C₂H₅ | SCH₃ | H | C₂H₅ |
| H | i-C₃H₇ | SCH₃ | H | C₂H₅ |
| H | i-C₃H₇ | Cl | H | C₂H₅ |
| H | i-C₃H₇ | Cl | H |  |
| H | C₂H₅ | Cl | H | C₂H₅ |
| H | C₂H₅ | Cl | H | —C(CH₃)₂—CN |
| H | i-C₃H₇ | Cl | H | i-C₃H₇ |

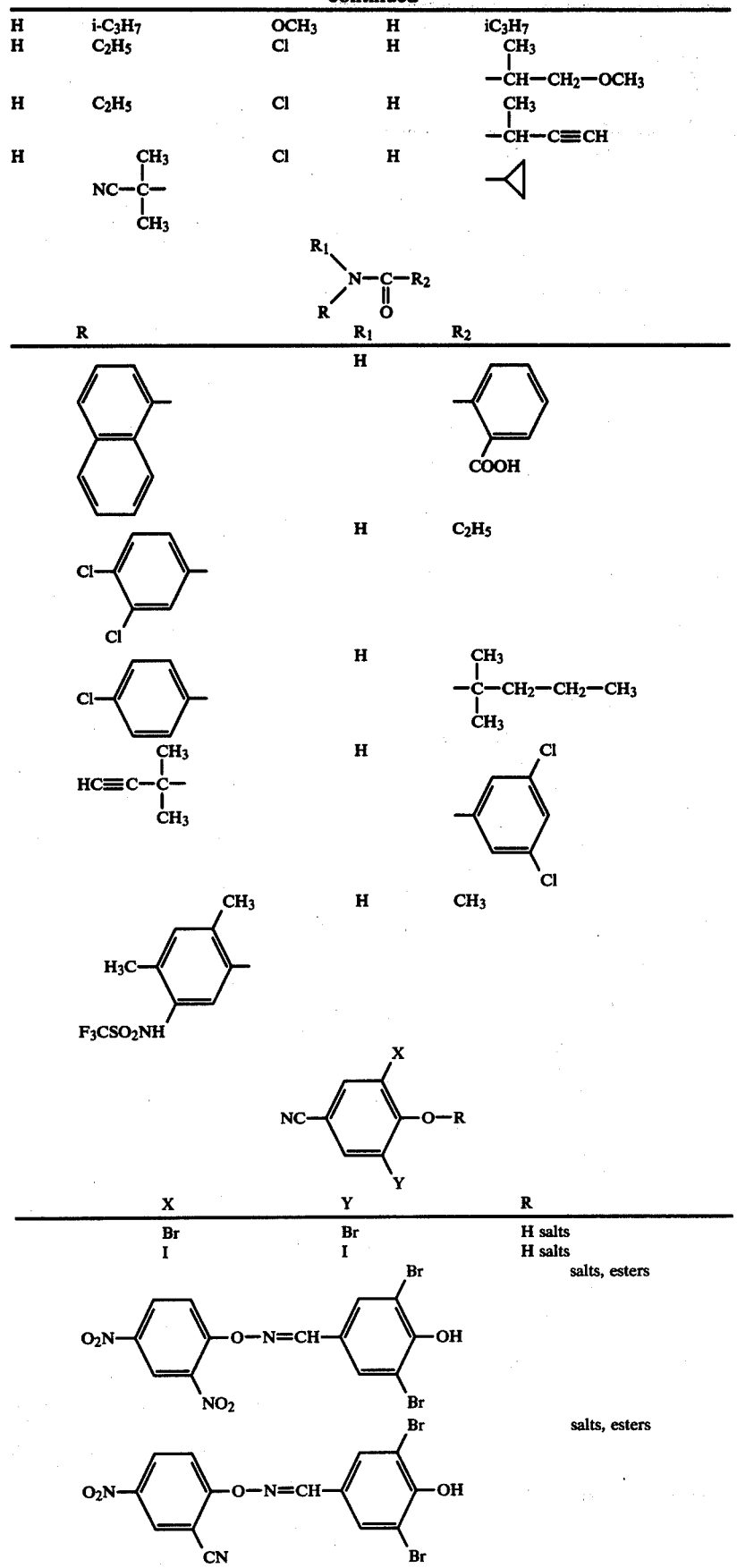

-continued $$\underset{R}{R_1}N-\underset{O}{\overset{\|}{C}}-\underset{R_3}{N}R_2$$

| R | R₁ | R₂ | R₃ |
|---|----|----|----|
| i-H₇C₃—C₆H₄— | H | CH₃ | CH₃ |
| 3-Cl-4-CH₃O—C₆H₃— | H | CH₃ | CH₃ |
| 2-benzothiazolyl | CH₃ | CH₃ | H |
| 4-(4-Cl-C₆H₄-O)—C₆H₄— | H | CH₃ | CH₃ |
| 3-F₃C—C₆H₄— | H | CH₃ | CH₃ |
| 4-Cl—C₆H₄— | H | CH₃ | —CH(CH₃)—C≡CH |
| 4-Br—C₆H₄— | H | CH₃ | OCH₃ |
| 4-Cl—C₆H₄— | H | CH₃ | OCH₃ |
| cyclooctyl | H | CH₃ | CH₃ |
| 3,4-Cl₂—C₆H₃— | H | CH₃ | OCH₃ |
| 3-Cl-4-Br—C₆H₃— | H | CH₃ | OCH₃ |
| 3-Cl-4-CH₃—C₆H₃— | H | CH₃ | CH₃ |
| 2-CF₃-5-(1,3,4-thiadiazolyl) | CH₃ | CH₃ | H |

-continued
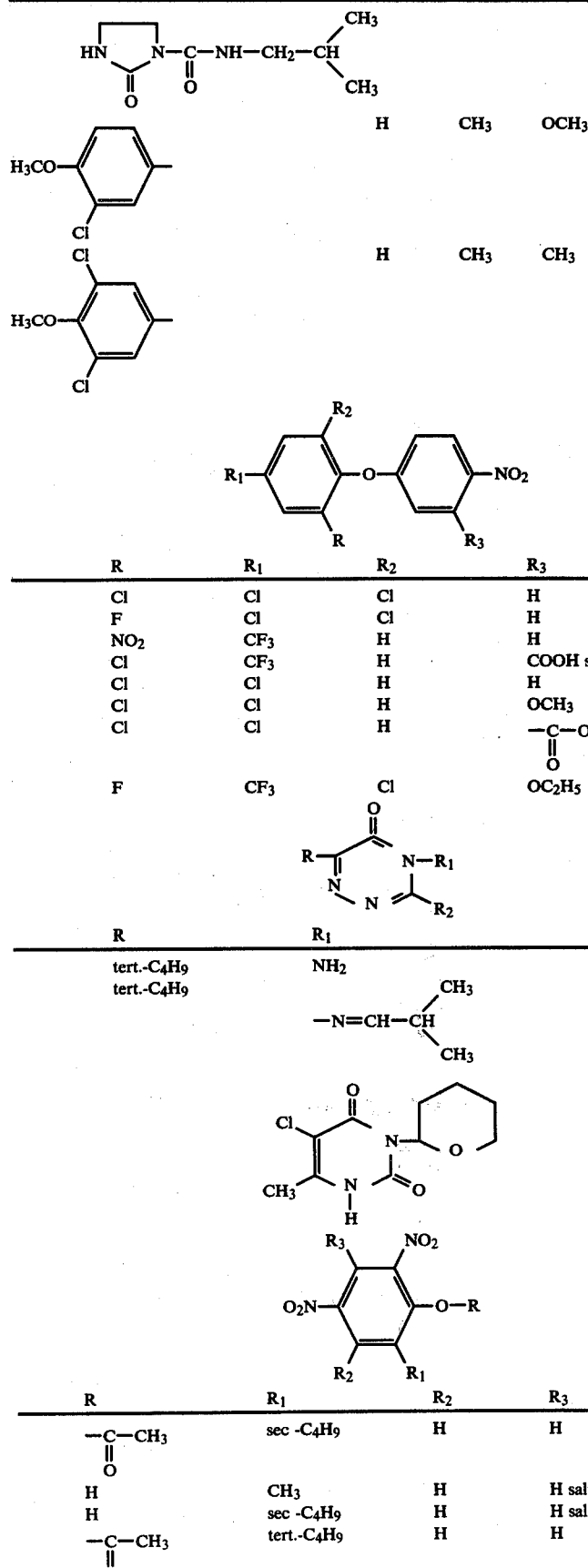
| R | R₁ | R₂ | R₃ |
|---|---|---|---|
| Cl | Cl | Cl | H |
| F | Cl | Cl | H |
| NO₂ | CF₃ | H | H |
| Cl | CF₃ | H | COOH salts |
| Cl | Cl | H | H |
| Cl | Cl | H | OCH₃ |
| Cl | Cl | H | —C(=O)—OCH₃ |
| F | CF₃ | Cl | OC₂H₅ |
| R | R₁ | R₂ |
|---|---|---|
| tert.-C₄H₉ | NH₂ | SCH₃ |
| tert.-C₄H₉ | —N=CH—CH(CH₃)₂ | SCH₃ |
| R | R₁ | R₂ | R₃ |
|---|---|---|---|
| —C(=O)—CH₃ | sec-C₄H₉ | H | H |
| H | CH₃ | H | H salts, esetrs |
| H | sec-C₄H₉ | H | H salts, esters |
| —C(=O)—CH₃ | tert.-C₄H₉ | H | H |

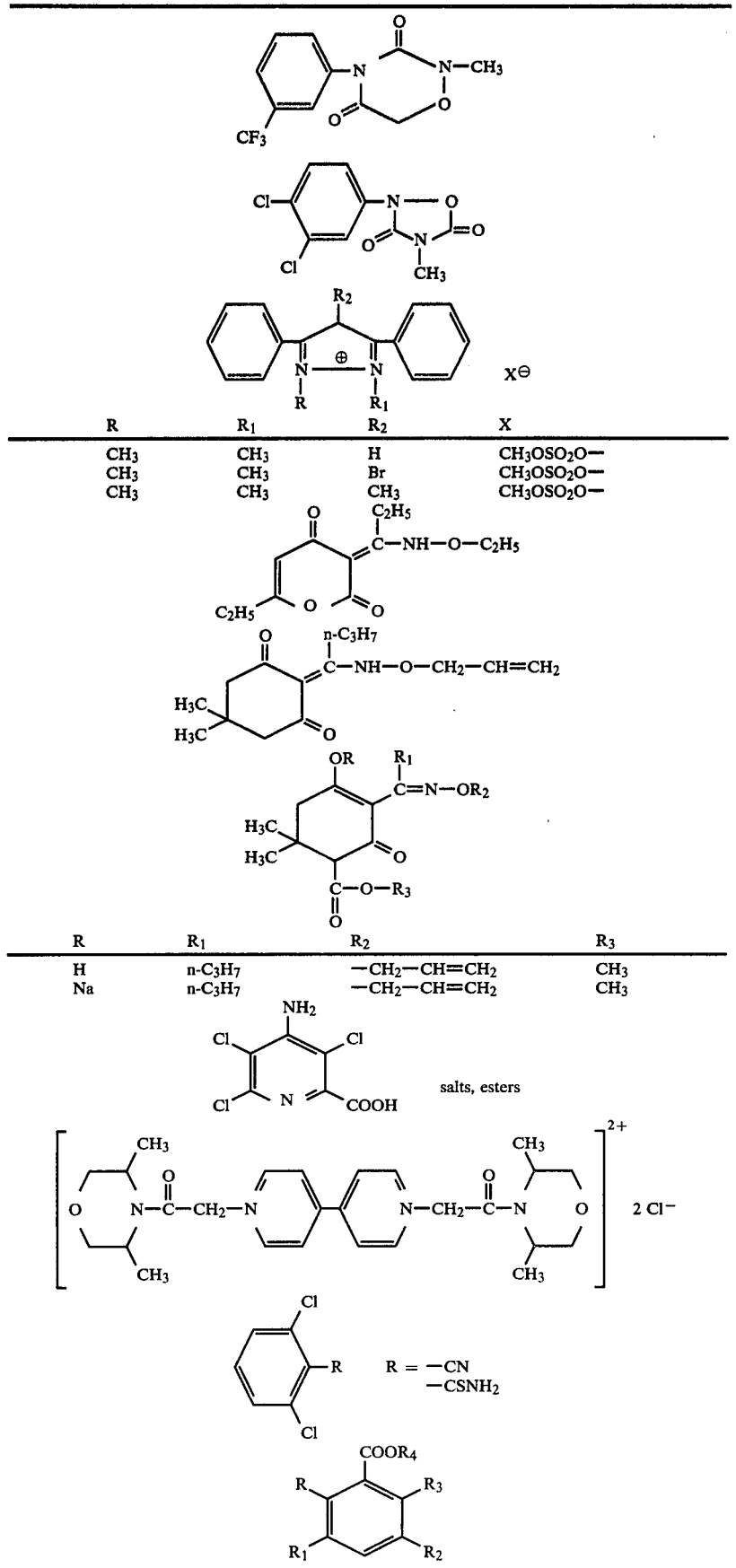

-continued
| R | R₁ | R₂ | R₃ | R₄ |
|---|----|----|----|----|
| Cl | H | Cl | OCH₃ | H salts, esters, amides |
| Cl | Cl | H | Cl | H . (CH₃)₂NH |
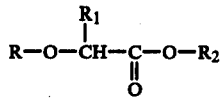
| R | R₁ | R₂ |
|---|----|----|
| 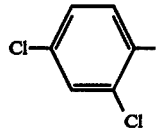 | CH₃ | H salts, esters, amides |
| 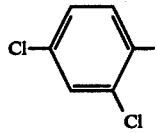 | H | H salts, esters, amides |
| 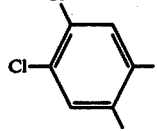 | H | H salts, esters, amides |
| 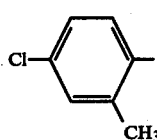 | H | H salts, esters, amides |
| 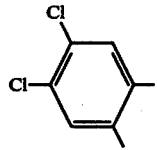 | CH₃ | H salts, esters, amides |
| 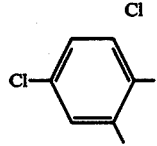 | CH₃ | H salts, esters, amides |
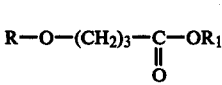
| R | R₁ |
|---|----|
| 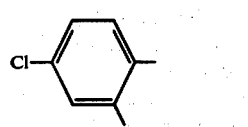 | H salts, esters, amides |
| 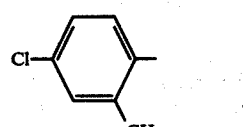 | H salts, esters, amides |
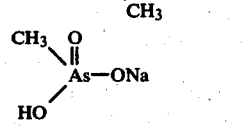
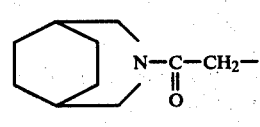

-continued

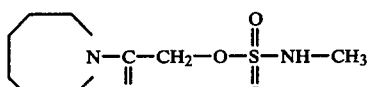

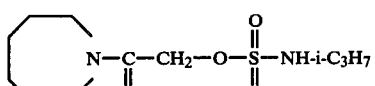

salts, esters

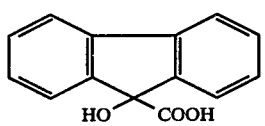

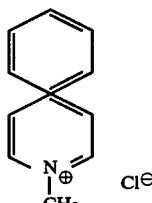

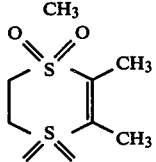

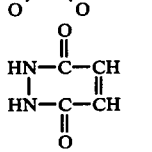

salts

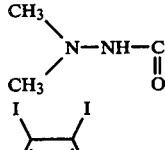

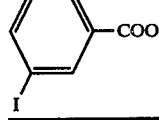

salts, esters, amides

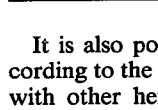

It is also possible to apply the new compounds according to the invention, either alone or in combination with other herbicides, in admixture with other crop protection agents, e.g., agents for combatting pests or phytopathogenic fungi or bacteria. Of interest is also the fact that the compounds according to the invention may be mixed with mineral salt solutions used to eliminate nutritional and trace element deficiencies.

To ensure that the herbicidal action sets in, spreader-stickers and non-phytotoxic oils may be added.

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

EXAMPLE 9

90 parts by weight of compound 1 is mixed with 10 parts by weight of N-methyl-α-pyrrolidone. A mixture is obtained which is suitable for application in the form of very fine drops.

EXAMPLE 10

20 parts by weight of compound 1 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of compound 1 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 20 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 12

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 13

20 parts by weight of compound 1 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 14

3 parts by weight of compound 1 is intimately mixed with 97 parts by weight of particulate kaolin. A dust is obtained containing 3% by weight of the active ingredient.

EXAMPLE 15

30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 16

40 parts by weight of compound 1 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

EXAMPLE 17

20 parts of compound 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A compound of the formula

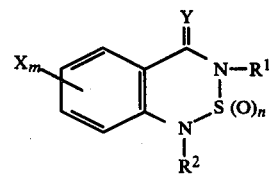

where $R^1$ is alkyl of 1 to 20 carbon atoms, lower haloalkyl, cycloalkyl of 3 to 7 carbon atoms, alkenyl of 2 to 11 carbon atoms, alkynyl of 2 to 8 carbon atoms, lower haloalkenyl, lower haloalkynyl, lower alkoxyalkyl, lower alkylmercaptoalkyl, lower alkyl- and dialkylcarbamoylalkyl, lower alkoxycarbonyl, lower alkoxycarboalkyl, lower alkoxycarboalkenyl, lower alkanoylalkyl, phenyl, phenyl substituted by halogen, methyl or halomethyl, or pyrrolidinyl, $R^2$ is CN, SCN, $$C(=NA)N\begin{matrix}R^4\\R^5\end{matrix},$$

$C(=N-OR^4)R^3$, $S(=O)OR^3$, $S(=O)_2OR^3$, $Si(R^6)_2R^7$, $$SO_2N\begin{matrix}R^8\\CH_2OR^9\end{matrix},$$

or $SCCl_2F$,

X is halogen, $NO_2$, lower alkyl, halo lower alkyl, cycloalkyl, benzyl, phenyl, CN, SCN, $CO_2R^3$, $$C(=O)N\begin{matrix}R^3\\R^4\end{matrix}, N\begin{matrix}R^3\\R^4\end{matrix},$$

$Y'R^4$, $SO_2R^3$, $SO_2OR^3$, $$SO_2N\begin{matrix}R^3\\R^4\end{matrix},$$

$CCl_3$, $CF_3$, $C(=O)R^3$ or $Y''CF_2C(Z)_3$, $R^3$ is hydrogen, lower alkyl, phenyl, or phenyl substituted by halogen, methyl or nitro, $R^4$ and $R^5$ being identical or different and each having the meanings of $R^3$ and are additionally, but not simultaneously, lower alkanoylalkyl, $R^6$ and $R^7$ being identical or different and each having the meanings of $R^3$ with the exception of hydrogen, $R^8$ and $R^9$ being identical or different and each having the meanings of $R^3$ with the exception of hydrogen and phenyl, A having the meanings of $R^3$ or is $OR^3$, $N(R^3)_2$, $OC(=O)NHR^3$ or $OC(=O)R^3$, each Y, Y' and Y'' is independently hydrogen, oxygen or sulfur, each Z is independently hydrogen, fluorine, bromine, chlorine or iodine, m is one of the integers 0, 1, 2, 3 and 4, and n is the integer 2.

2. 1-Cyano-3-n-propyl-2,1,3-benzothiadiazin-(4)-one-2,2-dioxide.

3. 1-Cyano-3-isopropyl-2,1,3-benzothiadiazin-(4)-one-2,2-dioxide.

4. 1-Cyano-3-sec-butyl-2,1,3-benzothiadiazin-(4)-one-2,2-dioxide.

5. 1-Cyano-3-cyclohexyl-2,1,3-benzothiadiazin-(4)-one-2,2-dioxide.

6. 1-Cyano-3-β-chloroethyl-2,1,3-benzothiadiazin-(4)-one-2,2-dioxide.

7. 1-Cyano-3-isopropyl-8-methyl-2,1,3-benzothiadiazin-(4)-one-2,2-dioxide.

8. 1-Cyano-3-isopropyl-6-bromo-2,1,3-benzothiadiazin-(4)-one-2,2-dioxide.

9. 1-Cyano-3-isopropyl-8-chloro-2,1,3-benzothiadiazin-(4)-one-2,2-dioxide.

10. 1-Cyano-3-isopropyl-8-methoxy-2,1,3-benzothiadiazin-(4)-one-2,2-dioxide.

11. 1-Cyano-3-isopropyl-8-fluoro-2,1,3-benzothiadiazin-(4)-one-2,2-dioxide.

12. A process for controlling the growth of unwanted plants which comprises treating the plants or soil with a compound of the formula where $R^1$ is alkyl of 1 to 20 carbon atoms, lower haloalkyl, cycloalkyl of 3 to 7 carbon atoms, alkenyl of 2 to 11 carbon atoms, alkynyl of 2 to 8 carbon atoms, lower haloalkenyl, lower haloalkynyl, lower alkoxyalkyl, lower alkylmercaptoalkyl, lower alkyl- and dialkylcarbamoylalkyl, lower alkoxycarbonyl, lower alkoxycarboalkyl, lower alkoxycarboalkenyl, lower alkanoylalkyl, phenyl, phenyl substituted by halogen, methyl or halomethyl, or pyrrolidinyl, $R^2$ is CN, SCN, $$C(=NA)N\begin{matrix}R^4\\R^5\end{matrix},$$

$C(=N-OR^4)R^3$, $S(=O)OR^3$, $S(=O)_2OR^3$, $Si(R^6)_2R^7$, $$SO_2N\begin{matrix}R^8\\CH_2OR^9\end{matrix},$$

or $SCCl_2F$,

X is halogen, $NO_2$, lower alkyl, halo lower alkyl, cycloalkyl, benzyl, phenyl, CN, SCN, $CO_2R^3$, $$C(=O)N\begin{matrix}R^3\\R^4\end{matrix}, N\begin{matrix}R^3\\R^4\end{matrix},$$

$Y'R^4$, $SO_2R^3$, $SO_2OR^3$, $$SO_2N\begin{matrix}R^3\\R^4\end{matrix},$$

$CCl_3$, $CF_3$, $C(=O)R^3$ or $Y''CF_2C(Z)_3$, $R^3$ is hydrogen, lower alkyl, phenyl, or phenyl substituted by halogen, methyl or nitro, $R^4$ and $R^5$ being identical or different and each having the meanings of $R^3$ and are additionally, but not simultaneously, lower alkanoylalkyl, $R^6$ and $R^7$ being identical or different and each having the meanings of $R^3$ with the exception of hydrogen, $R^8$ and $R^9$ being identical or different and each having the meanings of $R^3$ with the exception of hydrogen and phenyl, A having the meanings of $R^3$ or is $OR^3$, $N(R^3)_2$, $OC(=O)NHR^3$ or $OC(=O)R^3$, each Y, Y' and Y'' is independently hydrogen, oxygen or sulfur, each Z is independently hydrogen, fluorine, bromine, chlorine or iodine, m is one of the integers 0, 1, 2, 3 and 4, and n is the integer 2.

* * * * *